(12) United States Patent
Inagaki et al.

(10) Patent No.: US 10,717,872 B2
(45) Date of Patent: Jul. 21, 2020

(54) POLYETHER-POLYSILOXANE BLOCK COPOLYMER COMPOSITION, SURFACTANT AND FOAM STABILIZER INCLUDING SAME, POLYURETHANE FOAM-FORMING COMPOSITION, COSMETIC, AND PREPARATION METHOD THEREOF

(71) Applicant: Dow Corning Toray Co., Ltd., Tokyo (JP)

(72) Inventors: Hiroyuki Inagaki, Chiba (JP); Ikutaro Morikawa, Chiba (JP); Son Thanh Phan, Chiba (JP); Seiki Tamura, Chiba (JP)

(73) Assignee: DOW TORAY CO., LTD., Tokyo (JP)

( * ) Notice: Subject to any disclaimer, the term of this patent is extended or adjusted under 35 U.S.C. 154(b) by 0 days.

(21) Appl. No.: 15/566,112

(22) PCT Filed: Apr. 13, 2016

(86) PCT No.: PCT/JP2016/002004
§ 371 (c)(1),
(2) Date: Jan. 19, 2018

(87) PCT Pub. No.: WO2016/166979
PCT Pub. Date: Oct. 20, 2016

(65) Prior Publication Data
US 2019/0233646 A1 Aug. 1, 2019

(30) Foreign Application Priority Data
Apr. 14, 2015 (JP) .................... 2015-082742

(51) Int. Cl.
| | | |
|---|---|---|
| *C08L 83/12* | (2006.01) | |
| *A61K 8/894* | (2006.01) | |
| *C08G 77/46* | (2006.01) | |
| *C08K 5/05* | (2006.01) | |
| *C08G 18/48* | (2006.01) | |
| *C08G 18/79* | (2006.01) | |
| *C08G 18/28* | (2006.01) | |
| *C08G 18/76* | (2006.01) | |
| *C08G 18/22* | (2006.01) | |

(Continued)

(52) U.S. Cl.
CPC .............. *C08L 83/12* (2013.01); *A61K 8/046* (2013.01); *A61K 8/87* (2013.01); *A61K 8/894* (2013.01); *C08G 18/14* (2013.01); *C08G 18/1808* (2013.01); *C08G 18/222* (2013.01); *C08G 18/2835* (2013.01); *C08G 18/4829* (2013.01); *C08G 18/63* (2013.01); *C08G 18/638* (2013.01); *C08G 18/7664* (2013.01); *C08G 18/797* (2013.01); *C08G 77/46* (2013.01); *C08K 5/05* (2013.01); *C08K 5/06* (2013.01); *C08L 71/02* (2013.01); *C08L 75/04* (2013.01); *C08G 18/0852* (2013.01); *C08G 18/4833* (2013.01); *C08G 2101/0025* (2013.01); *C08G 2101/0083* (2013.01); *C08L 2203/14* (2013.01)

(58) Field of Classification Search
CPC ....... C08L 83/12; C08L 75/04; C08L 2203/14
See application file for complete search history.

(56) References Cited

U.S. PATENT DOCUMENTS 4,150,048 A * 4/1979 Schilling, Jr. .......... C08G 77/46
   521/112
4,242,466 A 12/1980 Schilling, Jr. et al.
(Continued)

FOREIGN PATENT DOCUMENTS

EP      0314903 A2    5/1989
JP      H01101333 A   4/1989
(Continued)

OTHER PUBLICATIONS

PCT/JP2016/002004 International Search Report dated Jun. 14, 2016, 2 pages.
English language abstract and machine translation for JPH0790102 (A) extracted from http://worldwide.espacenet.com database on Oct. 9, 2017, 11 pages.
English language abstract and machine translation for JPH07316010 (A) extracted from http://worldwide.espacenet.com database on Jan. 9, 2018, 16 pages.

(Continued)

Primary Examiner — Margaret G Moore
(74) Attorney, Agent, or Firm — Warner Norcross + Judd LLP

(57) ABSTRACT

A polyether-polysiloxane block copolymer composition is disclosed. The copolymer composition comprises (A) a polyether-polysiloxane block copolymer having in a molecule structural units as expressed by General Formula (1) below:

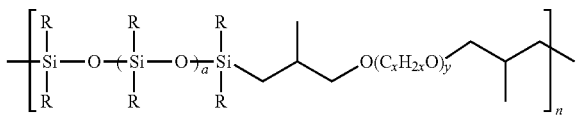

where a terminal group thereof is an alkenyl group or the like bonded to a polyether portion. The copolymer composition further comprises (B) a liquid monool organic compound, which is (B1) a glycol ether compound having a low degree of polymerization, a terminal hydrogen substituted with a hydrocarbon group, and a secondary alcoholic hydroxyl group provided on another terminal, or (B2) a higher alcohol compound having a branched alkyl group with 12 or more carbon atoms. The copolymer composition generally does not contain a dimethyl polysiloxane at more than the mass of component (A). A manufacturing method, foam stabilizer or the like containing the copolymer composition, and a polyurethane foam are also disclosed.

20 Claims, No Drawings

(51) Int. Cl.
*C08G 18/18* (2006.01)
*C08L 71/02* (2006.01)
*C08G 18/63* (2006.01)
*C08K 5/06* (2006.01)
*A61K 8/04* (2006.01)
*A61K 8/87* (2006.01)
*C08G 18/08* (2006.01)
*C08L 75/04* (2006.01)
*C08G 101/00* (2006.01)

(56) References Cited

U.S. PATENT DOCUMENTS

| | | | |
|---|---|---|---|
| 4,520,160 A * | 5/1985 | Brown | A61K 8/06 524/765 |
| 5,472,686 A | 12/1995 | Tsubaki et al. | |
| 5,660,819 A | 8/1997 | Tsubaki et al. | |
| 5,869,727 A | 2/1999 | Crane et al. | |
| 6,162,888 A | 12/2000 | Lee et al. | |
| 2004/0029986 A1 | 2/2004 | Ghobary et al. | |
| 2006/0029559 A1 | 2/2006 | Tamura | |
| 2007/0219318 A1* | 9/2007 | Lin | A61K 8/671 525/94 |
| 2008/0226708 A1* | 9/2008 | Lin | A61K 8/14 424/450 |
| 2009/0069457 A1 | 3/2009 | Brown et al. | |
| 2012/0101175 A1 | 4/2012 | Willoughby et al. | |
| 2012/0171148 A1 | 7/2012 | Tamura | |
| 2012/0245305 A1 | 9/2012 | Souda et al. | |
| 2012/0269875 A1 | 10/2012 | Tamura et al. | |
| 2013/0253215 A1 | 9/2013 | Moriya | |

FOREIGN PATENT DOCUMENTS

| | | |
|---|---|---|
| JP | H04211605 A | 8/1992 |
| JP | H04234307 A | 8/1992 |
| JP | H0790102 A | 4/1995 |
| JP | H07316010 A | 12/1995 |
| JP | H08156143 A | 6/1996 |
| JP | H11116670 A | 4/1999 |
| JP | 2000313730 A | 11/2000 |
| JP | 2000327785 A | 11/2000 |
| JP | 2002137234 A | 5/2002 |
| JP | 2005060876 A | 3/2005 |
| JP | 2005534770 A | 11/2005 |
| JP | 2006282820 A | 10/2006 |
| JP | 2007186557 A | 7/2007 |
| JP | 2009265425 A | 11/2009 |
| JP | 2010195870 A | 9/2010 |
| JP | 2010247532 A | 11/2010 |
| JP | 2010535931 A | 11/2010 |
| JP | 2010539280 A | 12/2010 |
| JP | 2011116902 A | 6/2011 |
| JP | 2012082273 A | 4/2012 |
| JP | 2012153802 A | 8/2012 |
| JP | 2012246397 A | 12/2012 |
| JP | 2013194218 A | 9/2013 |
| WO | WO2004058198 A1 | 7/2004 |
| WO | WO2011049248 A1 | 4/2011 |

OTHER PUBLICATIONS

English language abstract and machine translation for JPH08156143 (A) extracted from http://worldwide.espacenet.com database on Oct. 9, 2017, 13 pages.
English language abstract and machine translation for JP2000313730 (A) extracted from http://worldwide.espacenet.com database on Oct. 10, 2017, 13 pages.
English language abstract and machine translation for JP2002137234 (A) extracted from http://worldwide.espacenet.com database on Jan. 9, 2018, 20 pages.
English language abstract and machine translation for JP2005060876 (A) extracted from http://worldwide.espacenet.com database on Oct. 9, 2017, 23 pages.
English language abstract and machine translation for JP2006282820 (A) extracted from http://worldwide.espacenet.com database on Oct. 10, 2017, 13 pages.
English language abstract and machine translation for JP2007186557 (A) extracted from http://worldwide.espacenet.com database on Nov. 8, 2017, 23 pages.
English language abstract and machine translation for JP2009265425 (A) extracted from http://worldwide.espacenet.com database on Jan. 9, 2018, 13 pages.
English language abstract and machine translation for JP2010195870 (A) extracted from http://worldwide.espacenet.com database on Jan. 9, 2018, 19 pages.
English language abstract and machine translation for JP2010247532 (A) extracted from http://worldwide.espacenet.com database on Jan. 9, 2018, 24 pages.
English language abstract and machine translation for JP2012082273 (A) extracted from http://worldwide.espacenet.com database on Jan. 9, 2018, 17 pages.
English language abstract and machine translation for JP2012153802 (A) extracted from http://worldwide.espacenet.com database on Jan. 9, 2018, 18 pages.
English language abstract and machine translation for JP2012246397 (A) extracted from http://worldwide.espacenet.com database on Jan. 9, 2018, 13 pages.

* cited by examiner

POLYETHER-POLYSILOXANE BLOCK COPOLYMER COMPOSITION, SURFACTANT AND FOAM STABILIZER INCLUDING SAME, POLYURETHANE FOAM-FORMING COMPOSITION, COSMETIC, AND PREPARATION METHOD THEREOF

CROSS-REFERENCE TO RELATED APPLICATIONS

This application is the National Stage of International Application No. PCT/JP2016/002004 filed on 13 Apr. 2016, which claims priority to and all advantages of JP Patent Application No. 2015-082742 filed on 14 Apr. 2015, the content of which is hereby incorporated by reference.

TECHNICAL FIELD

The present invention relates to: a new polyether-polysiloxane block copolymer composition containing: (A) a polyether-polysiloxane block copolymer having a specific structure; and (B) a specific monool organic compound that is a liquid at 5° C., and not containing a dimethyl polysiloxane at more than the mass of component (A). Furthermore, the present invention relates to a surfactant, foam stabilizer (including a function as a foam controlling agent and foam stabilizing agent, same hereinafter), cosmetic raw material, and cosmetic containing the composition. Furthermore, the present invention relates to a polyurethane foam-forming composition containing the composition and polyurethane foam obtained therefrom.

BACKGROUND ART

A straight chain organopolysiloxane-polyether block copolymer obtained by hydrosilylation reacting (1) an organopolysiloxane containing a SiH group on both terminals and (2) a polyether containing a methallyl group on both terminals is known as (AB)n type polyether-modified silicone (Patent Literature 1). Furthermore, Patent Literature 2 reports a method of manufacturing polyurethane foam using a non-hydrolyzable straight chain organopolysiloxane-polyether block copolymer having a high degree of polymerization as a foam stabilizing agent. However, only a toluene solution obtained as a result of performing a hydrosilylation reaction in a toluene solvent exists as an example of a composition containing the block copolymer. Toluene has high hazardous properties, flammability, and other risks, and therefore is removed from a manufacturing system by a stripping treatment under heating or reduced pressure conditions. Similarly, a xylene solution containing the block copolymer is known or commercialized, but similarly has a problem of including a flammable and hazardous organic solvent.

Furthermore, several reports have been made in relation to an application of the (AB)n type polyether-modified silicone (Patent Literatures 3 to 8). Patent Literatures 3 and 4 relate to a cosmetic containing the (AB)n type polyether-modified silicone, and disclose an example of adding to several cosmetic product formulations silicone after performing synthesis of the modified silicone in toluene and then removing the toluene similar to Patent Literatures 1 and 2. Furthermore, the present text describes that the copolymer is used independently or dissolved in water or various organic solvents. Similarly, Patent Literature 5 and Patent Literature 6 disclose a substance where the (AB)n type polyether-modified silicone is synthesized in toluene or other organic solvent, used as a foam stabilizer (foam stabilizing agent) of urethane foam, the toluene or the like must be removed from the manufacturing system by a stripping treatment. Note that in addition to disclosing an example where synthesis of the copolymer is performed in toluene, polypropylene glycol which is a diluting agent is added, and then the toluene is removed by a stripping operation, Patent Literature 6 mentions that polyols used in a urethane foam formulation can be used as a diluting agent. Furthermore, a commercially available foam stabilizer using a long chain alkylene benzene as a reaction solvent is described as a comparative example.

However, as described in Patent Literature 6, after a hydrosilylation is performed in toluene, when a polypropylene glycol as a diluting agent or derivative thereof is added, the toluene is removed by reduced pressure stripping, and solvent exchanging is performed, the (AB)n type polyether-modified silicone will have excellent foam stability, and therefore, air bubbles caught by stirring are fine and very stable, defoaming is suppressed, an upper space of a reactor is immediately filled with foam, and a pressure reduction operation must be very slowly and gradually performed. In other words, the manufacturing method is disadvantageous in industrial mass production. In contrast, Patent Literature 6 discloses a foam stabilizer that is synthesized by a long chain alkylene benzene and then used as is, but there is a problem where the non-reactive solvent remains in urethane foam migrates (oozes out) from the final product.

In other words, not only is there no description that a specific monool organic compound is used in the (AB)n type polyether-modified silicone solvent, and the advantages thereof are not suggested in Literatures 1 to 6, there are problems in industrial production processes, and thus sufficient performance cannot be achieved.

Herein, Patent Literature 7 relates to a hair cosmetic including a specific structure with a particularly high molecular weight of the (AB)n type polyether-modified silicones. Herein, examples of adding the structure to a large number of cosmetic formulations is disclosed, and in many of these formulations, an excess amount of dimethyl polysiloxane is combined with the structure. Patent Literature 8 relates to a straight oil agent for a fiber filamentous material including: a specific structure with a particularly high molecular weight of the (AB)n type polyether-modified silicones, and base oil formed from at least one type selected from diorganopolysiloxanes and mineral oils. With this application, continuous high speed processing of the fiber filamentous material is important in the process, and the viscosity of the oil agent must be kept low at a maximum of 100 mm$^2$/s (and preferably 50 mm$^2$/s) or lower. Therefore, in this example, a 10 mm$^2$/s dimethyl polysiloxane is excessively mixed at over 40 times the structure and then used. In other words, the literatures only disclose a composition where dimethyl polysiloxane is excessively added to the (AB)n type polyether-modified silicone, and in each application, the dimethyl polysiloxane must be included at a large amount. In other words, there is no mention nor suggestion that the amount of dimethyl polysiloxane is at a constant level or lower and the advantages thereof, in the composition containing the (AB)n type polyether-modified silicone.

Similarly, Patent Literature 9 discloses a technique for stably manufacturing a copolymer with a particularly high molecular weight of the (AB)n type polyether-modified silicones or resembling structures, without causing increased viscosity, gelling, and the like. One of the examples describes synthesizing the copolymer in liquid isoparaffin (hydrogenated polyisobutene), and then distilling a low-boiling substance such as an unreacted substance by stripping (under heated and reduced pressure conditions). Furthermore, the present text describes several organic solvents and dimethyl polysiloxanes as a solvent that can be used in a hydrosilylation reacting step for synthesizing the copolymer. However, there is no mention nor suggestion that a specific monool organic compound is used in a solvent of the (AB)n type polyether-modified silicone, the amount of dimethyl polysiloxanes is at a constant level or lower in the composition, and the advantages thereof.

In other words, the compositions disclosed in Patent Literatures 1 to 9 are compositions that cannot be used in a surfactant or foam stabilizer of urethane, are inevitably disadvantageous in industrial production in a step of replacing a solvent obtained by synthesizing in an organic solvent with high toxicity such as toluene or the like with propylene glycol or the like, or have problems in performance as a foam stabilizer, and thus there is room for improvement in performance and manufacturing cost thereof. Therefore, the compositions are not sufficiently satisfactory for use as a surfactant or foam stabilizer, and thus had a problem where widespread adoption was hindered due to performance and cost.

On the other hand, Patent Literature 10 points out the importance of a surfactant with a high open cell effect in both hard foam and soft foam in open cell polyurethane foam and manufacturing process thereof, and points out the importance of controlling the open cell ratio even in the field of high density microcellular foam. However, Patent Literature 10 points out that a known (AB)n type polyether-modified silicone (=(AB)n copolymer) in the related art tends to form hydrogel in the presence of water, and therefore, use is limited. This is considered to indicate that a raw material composition for obtaining polyurethane foam has disadvantages of inferior storage stability of a so-called premixed solution formed from components other than isocyanate (including polyols, water, catalyst, and optionally, surfactants, and the like), and hard to be existing in a homogeneous condition for a long period of time.

The (AB)n type polyether-modified silicone can be designed to have an average molecular weight of a copolymer, and the surface activation performance, affinity to a urethane foam system, and the like can be controlled by the EO % or size of a polyether portion or by introducing a hydrophobic group or hydroxyl group to a terminal portion of a copolymer, and therefore is thought to be able to demonstrate an excellent effect as a surfactant for foam stabilization or foam control, in all polyurethane foam formulations other than high resilience foam which requires a foam stabilizer with a low molecular weight. In particular, the silicone is very useful in suppressing the open cell ratio required in recent years. However, known technology in the related art has the aforementioned problems with performance, manufacturing problems directly linked to industrial production cost, problems with application, and problems such as insufficient penetration into the market regardless of potential value due to these factors. Therefore, development is desired for a new composition containing the (AB)n type polyether-modified silicone having sufficient usefulness in applications such as surfactants, foam stabilizers, and the like, which can resolve the plurality of problems and be supplied into the market in a larger amount and lower cost than in the related art.

PRIOR ART DOCUMENTS

Patent Documents

Patent Literature 1: U.S. Pat. No. 4,150,048
Patent Literature 2: U.S. Pat. No. 4,242,466
Patent Literature 3: JP 04-211605 A (U.S. Pat. No. 5,660, 819)
Patent Literature 4: JP 04-234307 A (U.S. Pat. No. 5,472, 686)
Patent Literature 5: JP 07-090102 A (JP 3319833 B)
Patent Literature 6: JP 08-156143 A
Patent Literature 7: WO 2004/058198 (U.S. Pat. No. 8,114, 391)
Patent Literature 8: JP 2005-060876 A
Patent Literature 9: JP 2006-282820 A (JP 4875314 B)
Patent Literature 10: JP 2010-539280 T (U.S. Pat. No. 8,436,064)
Patent Literature 11: WO 2011/049248 (U.S. Pat. No. 8,784, 787)

SUMMARY OF THE INVENTION

Problems to be Solved by the Invention

In order to resolve the aforementioned problems, an object of the present invention is to provide: a new polyether-polysiloxane block copolymer composition that is not only a foam stabilizing agent and can control an open cell ratio, has excellent homogeneity and stability in a premixed solution, and has excellent phase solubility with various components in a foam-forming emulsion composition, even in fields such as high-density microcellular foam by a mechanical foaming method, other hard foams or soft foams, and the like; a surfactant containing the composition; and foam stabilizer containing the composition. Similarly, an object is to provide a cosmetic raw material containing the composition, and a cosmetic.

Furthermore, an object of the present invention is to provide a polyurethane foam-forming composition containing the polyether-polysiloxane block copolymer composition, and polyurethane foam prepared thereby.

Furthermore, an object of the present invention is to provide a method of manufacturing the polyether-polysiloxane block copolymer composition, which can be supplied to the market in mass amounts at a lower cost than in the related art.

Means for Solving the Problems

As a result of extensive studies in order to resolve the aforementioned problems, the present inventors discovered that the aforementioned problems can be resolved by:
(A) a polyether-polysiloxane block copolymer having a specific structural unit, where a terminal group (—Z) thereof is one type or more functional group selected from $Z^1$: alkenyl groups, hydroxyl groups, alkoxy groups, or acetoxy groups bonded to a polyether portion and $Z^2$: monovalent hydrocarbon groups that do not have a hetero atom, hydroxyl groups, or alkoxy groups; and
(B) a polyether-polysiloxane block copolymer composition selected from (B1) glycol ether compounds where a terminal hydrogen is substituted by a hydrocarbon group with 1 to 8 carbon atoms, a secondary alcoholic hydroxyl group is provided on another terminal, and the repeating number of oxyalkylene units with 2 to 4 carbon atoms is a number within a range of 1 to 3, and (B2) higher alcohol compounds having a branched alkyl group with 12 or more carbon atoms, that is a liquid at 5°, and which has one alcoholic hydroxyl group in a molecule, does not contain a hetero atom other than oxygen, contains one type or two or more types of monool organic compounds at a mass ratio of (A)/(B)=10/90 to 90/10, and does not contain a dimethyl polysiloxane at more than the mass of component (A), thereby achieving the present invention. Furthermore, the present inventors discovered that the aforementioned problems can be preferably resolved by a polyether-polysiloxane block copolymer composition further containing (C) at least one type of polyalkylene glycol or derivative thereof, which is a liquid at 25° C., where one terminal hydroxyl group may be substituted by a hydrocarbon group with 1 to 8 carbon atoms selected from alkyl, aralkyl, and aryl groups, and the repeating number of oxyalkylene units with 2 to 4 carbon atoms is within a range of 4 to 50, within a range of 10 to 300 parts by mass with regard to a total of 100 parts by mass of component (A) and component (B), where the viscosity at 25° C. of the entire composition is within a range of 100 to 35000 mm$^2$/s, thereby achieving the present invention.

Furthermore, the present inventors discovered that the aforementioned problems can be preferably resolved by a surfactant, foam stabilizer, polyurethane foam-forming composition, cosmetic raw material, or cosmetic containing the composition, thereby achieving the present invention. Furthermore, the present inventors discovered that the aforementioned problems can be preferably resolved by polyurethane foam obtained by the aforementioned polyurethane foam-forming composition.

Furthermore, the present inventors discovered that the aforementioned problems can be preferably resolved by a method of manufacturing of a polyether-polysiloxane block copolymer composition, at least including at least a step selected from steps of initiating or promoting hydrosilylation between a specific organopolysiloxane containing a SiH group on both terminals and a specific polyether containing a methallyl group on both terminals of a molecular chain (1) essentially in the absence of a solvent,
(2) in the presence of a monool organic compound which is the aforementioned component (B), or
(3) in the presence of a volatile organic solvent (B') different from the aforementioned component (B)
where in the case of (1) or (3), at least a step of performing solvent exchange with the monool organic compound which is the aforementioned component (B) is further included, thereby achieving the present invention.

In other words, the objects of the present invention are achieved by:
(1) A polyether-polysiloxane block copolymer composition, containing the following component (A) and component (B) at a mass ratio of (A)/(B)=10/90 to 90/10, and not containing a dimethyl polysiloxane at more than the mass of component (A):
(A) a polyether-polysiloxane block copolymer having a molecule structural units as expressed by General Formula (1) below:

[Chemical Formula 1]

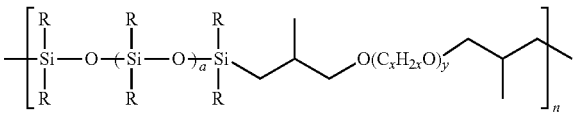

(where R individually represent a monovalent hydrocarbon group with 1 to 9 carbon atoms, which does not have an aliphatic unsaturated bond; x represents a number from 2 to 4; a represents a number from 1 to 200; y represents a number where the molecular weight of a polyether portion as expressed by (CxH2xO)y is within a range of 400 to 5000; and n represents a number of at least 2), wherein a terminal group (—Z) thereof is at least one type of functional group selected from $Z^1$: alkenyl groups, hydroxyl groups, alkoxy groups, or acetoxy groups bonded to a polyether portion; and $Z^2$: monovalent hydrocarbon groups that do not have a hetero atom, hydroxyl groups, or alkoxy groups, bonded to a silicon atom; (B) One or two or more types of monool organic compounds selected from the following (B1) or (B2), which is a liquid at 5° C., has one alcoholic hydroxyl group in a molecule, and does not contain a hetero atom other than oxygen: (B1) glycol ether compounds where a terminal hydrogen is substituted by a hydrocarbon group with 1 to 8 carbon atoms, a secondary alcoholic hydroxyl group is provided on another terminal, and the repeating number of oxyalkylene units with 2 to 4 carbon atoms is a number within a range of 1 to 3, and (B2) higher alcohol compounds having a branched alkyl group with 12 or more carbon atoms.

(1-1) a polyether-polysiloxane block copolymer composition according to (1), wherein component (A) is a polyether-polysiloxane block copolymer where the aforementioned terminal group (—Z) does not include an epoxy group, and a portion thereof may be a residual group of a monool organic compound derived from the aforementioned component (B); and (1-2) a polyether-polysiloxane block copolymer composition according to (1), essentially not containing a dimethyl polysiloxane.

The objects of the present invention are preferably achieved by the following composition:

(2) the polyether-polysiloxane block copolymer composition according to (1), wherein in the aforementioned general formula of component (A), a represents a number within a range of 10 to 45, y represents a number where the molecular weight of a polyether portion as expressed by (CxH2xO)y is within a range of 2000 to 5000, and the mass ratio of an oxyethylene ($C_2H_4O$) unit configuring the entire polyether portion is within a range of 35 to 90% on average;

(3) the polyether-polysiloxane block copolymer composition according to (1) or (2), wherein component (A) is a polyether-polysiloxane block copolymer obtained by hydrosilylation reacting an organopolysiloxane containing a SiH group on both terminals as expressed by General Formula (2):

[Chemical Formula 2]

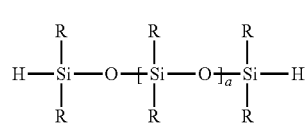

(where R represents the same groups as described above, and a represents the same numbers as described above), and a polyether containing a methallyl group on both terminals as expressed by General Formula (3) below:

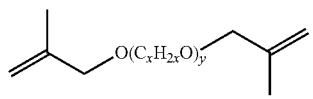

(where x and y represent the same numbers as described above), and having structural units as expressed by General Formula (1):

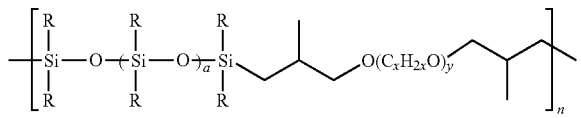

(where R represents the same groups as described above, and x, a, y, and n represent the same numbers as described above);
(4) a polyether-polysiloxane block copolymer composition according to any one of (1) to (3), wherein component (B) is a monool organic compound having a boiling point where distillation or purification by distilling is possible;
(5) the polyether-polysiloxane block copolymer composition according to any one of (1) to (4), wherein component (B) is one or two or more types of monool organic compound selected from propylene glycol monobutyl ethers, dipropylene glycol monobutyl ethers, tripropylene glycol monobutyl ethers, propylene glycol monomethyl ethers, dipropylene glycol monomethyl ethers, tripropylene glycol monomethyl ethers, propylene glycol mono(iso)propyl ethers, dipropylene glycol mono(iso)propyl ethers, tripropylene glycol mono(iso)propyl ethers, propylene glycol monoethyl ethers, dipropylene glycol monoethyl ethers, tripropylene glycol monoethyl ethers, 2-butyl-1-octanosl, 2-hexyl-1-decanols, 2-octyl-1-dodecanols, isostearyl alcohols, and 2-decyl-1-tetradecanols;
(6) The polyether-polysiloxane block copolymer composition according to any one of (1) to (5), wherein the mass ratio of the aforementioned component (A) and component (B) is within a range of 20/80 to 70/30;
(7) the polyether-polysiloxane block copolymer composition according to any one of (1) to (6), further containing: (C) at least one type of polyalkylene glycol or derivative thereof, which is a liquid at 25° C., where one terminal hydroxyl group may be substituted by a hydrocarbon group with 1 to 8 carbon atoms selected from alkyl, aralkyl, and aryl groups, and the repeating number of oxyalkylene units with 2 to 4 carbon atoms is within a range of 4 to 50, within a range of 10 to 300 parts by mass with regard to a total of 100 parts by mass of component (A), and component (B), wherein
the viscosity of the entire composition at 25° C. is within a range of 100 to 35000 mm$^2$/s; and (7-1) a polyether-polysiloxane block copolymer composition according to (7), wherein component (C) is one type or more selected from polyalkylene glycols where the repeating number of an oxyalkylene unit with 2 to 4 carbon atoms is within a range of 6 to 20, or derivative thereof.

Furthermore, the objects of the present invention are achieved by the following inventions containing the composition:
(8) a surfactant, containing the polyether-polysiloxane block copolymer composition according to any one of (1) to (7);
(9) a foam stabilizer, containing the polyether-polysiloxane block copolymer composition according to any one of (1) to (7);
(10) a polyurethane foam-forming composition, containing the polyether-polysiloxane block copolymer composition according to any one of (1) to (7);
(11) a polyurethane foam-forming composition, containing:
(a) a polyol;
(b) a polyisocyanate;
(c) a catalyst;
(d) a foam stabilizer containing the polyether-polysiloxane block copolymer composition according to any one of (1) to (7); and
(e) optionally, at least one added component selected from a group consisting of foam stabilizers other than component (d), foaming agents, diluting agents, chain extenders, crosslinking agents, water, nonaqueous foaming agents, fillers, reinforcing agents, pigments, dyes, coloring agents, flame retardants, antioxidants, anti-ozone agents, UV stabilizers, antistatic agents, disinfectants, and antibacterial agents.
(12) the polyurethane foam-forming composition according to (10) or (11), containing 0.5 to 8.0 parts by mass of the polyether-polysiloxane block copolymer (A) in the polyether-polysiloxane block copolymer composition according to any one of claims 1 to 7, with regard to 100 parts by mass of (a) the polyol;
(13) polyurethane foam obtained from the polyurethane foam-forming composition according to any one of (10) to (12);
(14) the polyurethane foam according to (13), which is hard foam, semi-hard foam, soft foam, or microcellular foam;
(15) cosmetic raw material, containing the polyether-polysiloxane block copolymer composition according to any one of (1) to (7); and
(16) cosmetic, containing the polyether-polysiloxane block copolymer composition according to any one of (1) to (7).

The objects of the present invention are particularly preferably achieved by the following manufacturing methods:
(17) a method of manufacturing the polyether-polysiloxane block copolymer composition according to any one of (1) to (7), at least including the steps of:
essentially initiating a hydrosilylation reaction between an organopolysiloxane containing a SiH group on both terminals as expressed by aforementioned General Formula (2) and a polyether containing a methallyl group on both terminals as expressed by the aforementioned General Formula (3), without a solvent; and diluting or promoting the reaction by adding the monool organic compound which is the aforementioned component (B).
(18) a method of manufacturing the polyether-polysiloxane block copolymer composition according to any one of (1) to (7), at least including the step of initiating or advancing the hydrosilylation reaction between an organopolysiloxane containing a SiH group on both terminals as expressed by aforementioned General Formula (2) and a polyether containing a methallyl group on both terminals as expressed by the aforementioned General Formula (3), in the presence of the monool organic compound which is the aforementioned component (B);
(19) a method of manufacturing the polyether-polysiloxane block copolymer composition according to any one of (1) to (7), at least including the steps of: initiating or advancing a hydrosilylation reaction between an organopolysiloxane containing a SiH group on both terminals as expressed by aforementioned General Formula (2) and a polyether containing a methallyl group on both terminals as expressed by the aforementioned General Formula (3), under the present of a volatile organic solvent (B') which is different from the aforementioned component (B);

and solvent exchanging the volatile organic solvent (B') which is different from the aforementioned component (B) with the monool organic compound which is the aforementioned component (B); and

(20) the method of manufacturing a polyether-polysiloxane block copolymer composition according to (17) or (18), wherein a stripping step is essentially not provided.

Effects of the Invention

The present invention can provide a new polyether-polysiloxane block copolymer composition that is not only the foam stabilizing agent and can control the open cell ratio, has excellent homogeneity and stability in a premixed solution, and has excellent phase solubility with various components in a foam-forming emulsion composition, even in fields such as high-density microcellular foam by a mechanical foaming method, other hard foams or soft foams, and the like. Furthermore, the present invention can provide a surfactant and foam stabilizer containing the composition. Similarly, the present invention can provide a cosmetic raw material containing the composition, and a cosmetic. In particular, a foam stabilizer containing the new polyether-polysiloxane block copolymer composition of the present invention has very high usefulness based on the aforementioned advantages.

Furthermore, the present invention can provide a polyurethane foam-forming composition containing the polyether-polysiloxane block copolymer composition, and polyurethane foam prepared thereby. Polyurethane foam obtained using the polyether-polysiloxane block copolymer composition of the present invention in a foam stabilizer is very useful.

Furthermore, the present invention can provide a method of manufacturing the polyether-polysiloxane block copolymer composition, which can be supplied to the market at a larger amount and lower cost than in the related art. Thereby, problems with the performance of a polyether-polysiloxane block copolymer composition, manufacturing problems directly linked to industrial production cost, and problems with application, which were difficult to overcome with technology in the related art can be comprehensively resolved, a new polyether-polysiloxane block copolymer composition can sufficiently penetrate into the market, and use as a high performance raw material is possible.

Mode for Carrying Out the Invention

A polyether-polysiloxane block copolymer composition of the present invention will be described below in detail. The present invention composition contains the following component (A) and component (B) at a mass ratio of (A)/(B)=10/90 to 90/10, and does not contain a dimethyl polysiloxane at more than the mass of component (A). First, each component will be described.

Component (A)

Component (A) is a polyether-polysiloxane block copolymer which is a main component of the present invention composition, having a structural unit as expressed by General Formula (1):

[Chemical Formula 3]

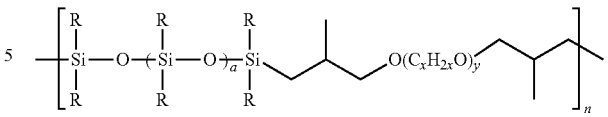

(where R individually represent a monovalent hydrocarbon group with 1 to 9 carbon atoms, which does not have an aliphatic unsaturated bond; x represents a number from 2 to 4; a represents a number from 1 to 200; y represents a number where the molecular weight of a polyether portion as expressed by $(C_xH_{2x}O)_y$ is within a range of 400 to 5000; and n represents a number of at least 2), where a terminal group (—Z) thereof is at least one type of functional group selected from $Z^1$: alkenyl groups, hydroxyl groups, alkoxy groups, or acetoxy groups bonded to a polyether portion; and $Z^2$: monovalent hydrocarbon groups that do not have a hetero atom, hydroxyl groups, or alkoxy groups, bonded to a silicon atom.

Component (A) is a polyether-polysiloxane block copolymer having the aforementioned specific structural unit, where a terminal group (—Z) thereof is one type or more functional groups selected from the aforementioned $Z^1$ and $Z^2$. Herein, from the perspective of use as a foam stabilizer and stability of the copolymer, one terminal or both terminals of the polyether-polysiloxane block copolymer is preferably blocked by a functional group including a polyether portion, and in this case, the terminal group (—Z) is preferably an alkenyl group, hydroxyl group, alkoxy group, or acetoxy group bonded to a polyether portion, and is particularly preferably a methallyl group. Note that the polyether-polysiloxane block copolymer where one terminal or both terminals is blocked by a functional group including a polyether portion can be easily synthesized by adding a polyether raw material containing a methallyl group or the like on both terminals to an organopolysiloxane containing a SiH group on both terminals such that the substance amount of methallyl groups in the polyether raw material is an equal or slightly excess amount with regard to the silicon-bonded hydrogen atoms in the organopolysiloxane containing a SiH group on both terminals, and then carrying out hydrosilylation reaction.

On the other hand, from the perspective of use as a foam stabilizer, stability of the copolymer, and safety, the terminal group (—Z) cannot include a reactive functional group having a hetero atom, and particularly cannot include a ring-opening reactive functional group which is an epoxy group, or an amine group or the like. Note that when the polyether-polysiloxane block copolymer is synthesized, in a case where the organopolysiloxane containing a SiH group on both terminals is used in the raw material, a portion of the terminal SiH may react with a monool organic compound described later, and thus a portion of the terminal groups (—Z) of a portion of component (A) of the present invention may be residual groups of a monool organic compound derived from the aforementioned component (B).

From the perspective of use as a foam stabilizer and handling properties of the copolymer, in the aforementioned General Formula (1), a is particularly preferably a number within a range of 10 to 45, y is particularly preferably a number where the molecular weight of a polyether (polyoxyalkylene) portion is within a range of 2000 to 4500, and the mass ratio of oxyethylene $C_2H_4O$ units configuring the entire polyether portion is particularly preferably within a range of 35 to 90% on average. In the aforementioned range, the hydrophilicity of the polyether-polysiloxane block copolymer is particularly improved, and a certain amount of oxypropylene units or oxybutylene units is inevitably included, and therefore, the range is advantageous for improving the compatibility between the foam stabilizer and polyol or isocyanate which is a main component of the polyurethane foam-forming composition, and for achieving increased convenience by improving the stability of a pre-mixed solution, a desirable foam stabilizing effect, or the like. Function as a surfactant or foam stabilizer and handling properties during synthesis or after synthesis are also improved.

In the aforementioned General Formula (1), R individually represents a monovalent hydrocarbon group with 1 to 9 carbon atoms that do not have an aliphatic unsaturated bond, and examples include alkyl groups with 1 to 9 carbon atoms. Methyl groups or ethyl groups are preferable. Industrially, methyl groups are particularly preferable.

The polyether-polysiloxane block copolymer can be synthesized by hydrosilylation reacting an organopolysiloxane containing a SiH group on both terminals with a polyether raw material having a carbon-carbon double bond such as a methallyl group or the like on both terminals of a molecular chain, in the presence or absence of an arbitrary solvent. As described above, one terminal or both terminals thereof are preferably blocked with a functional group including a polyether portion, and is particularly preferably synthesized by adding an amount of methallyl groups in the polyether raw material that is an equal or slightly excess amount with regard to the silicon-bonded hydrogen atoms in the organopolysiloxane containing a SiH group on both terminals, and carrying out hydrosilylation reaction.

More preferably, the polyether-polysiloxane block copolymer is particularly preferably a polyether-polysiloxane block copolymer obtained by a hydrosilylation reaction between an organopolysiloxane containing a SiH group on both terminals as expressed by General Formula (2) below:

[Chemical Formula 4]

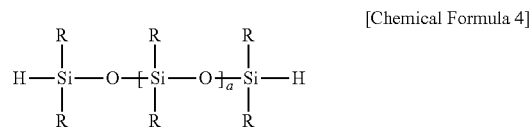

(where a represents the same numbers as described above), and a polyether containing a methallyl group on both terminals as expressed by General Formula (3) below:

[Chemical Formula 5]

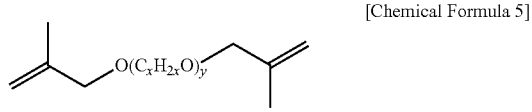

(where x and y represent the same numbers as described above).

Component (B)

Component (B) is a characteristic component of the present invention composition, is a liquid at 5° C., and is one or two or more types of a specific monool organic compound selected from the following (B1) or (B2) having one alcoholic hydroxyl group in a molecule, and not containing a hetero atom other than oxygen. The component (B) is a solvent of the polyether-polysiloxane block copolymer, which may be introduced to the composition as a solvent in the synthesis reaction, or may be introduced to the composition in a solvent-substituted or solvent-added form in a system after performing a synthesis reaction of the polyether-polysiloxane block copolymer in the presence or absence of another solvent.

In particular, component (B) is preferably a monool organic compound having a boiling point where distillation or purification by distilling is possible.

Component (B1) is a glycol ether compound where a terminal hydrogen is substituted by a hydrocarbon group with 1 to 8 carbon atoms, a secondary alcoholic hydroxyl group is provided on another terminal, and the repeating number of oxyalkylene units with 2 to 4 carbon atoms is a number within a range of 1 to 3, and the repeating number of oxyalkylene units needs to be a number within a range of 1 to 3, the degree of polymerization must be relatively low, a first terminal needs to be blocked by a hydrocarbon group, and a secondary alcoholic hydroxyl group needs to be on a second terminal. Examples of the compound include propylene glycol monobutyl ethers, dipropylene glycol monobutyl ethers, tripropylene glycol monobutyl ethers, propylene glycol monomethyl ethers, dipropylene glycol monomethyl ethers, tripropylene glycol monomethyl ethers, propylene glycol mono(iso)propyl ethers, dipropylene glycol mono(iso)propylene ethers, tripropylene glycol mono (iso)propyl ethers, propylene glycol monoethyl ethers, dipropylene glycol monoethyl ethers, tripropylene glycol monoethyl ethers, and the like. On the other hand, using a monool organic compound such as diethylene glycol monobutyl ether or the like having an alcoholic hydroxyl group other than a secondary group such as a primary alcoholic hydroxyl group on a terminal is inappropriate from the perspective of not being able to sufficiently achieve the technical effects of the present invention.

Component (B2) is a higher alcohol compound having a branched alkyl group with 12 or more carbon atoms, and examples of the compound include 2-butyl-1-octanols, 2-hexyl-1-decanols, 2-octyl-1-dodecanols, isostearyl alcohols, 2-decyl-1-tetradecanols, and the like. On the other hand, using higher alcohol compounds having a straight chain alkyl group is inappropriate from the perspective of easily solidifying or precipitating due to high melting points, from the perspective of mixtures easily separating due to inferior compatibility with the polyether-polysiloxane block copolymer, and from the perspective of not being able to sufficiently achieve the technical effects of the present invention.

Component (B) is a component that functions as a solvent (dispersing medium) of component (A), but in the composition of the present invention, it is important that the mass ratio of the components (A)/(B) is within a range of 10/90 to 90/10 from the perspective of performance, quality, convenience during use, handling workability (handling), and the like of the composition, and the mass ratio of (A)/(B) is preferably within a range of 20/80 to 70/30.

It is important that the polyether-polysiloxane block copolymer composition of the present invention containing the aforementioned component (A) and component (B) has a viscosity at 25° C. that is within a range of 100 to 60000 mm$^2$/s from the perspective of convenience during use, handling, and the like.

Furthermore, the polyether-polysiloxane block copolymer composition of the present invention primarily is a foam stabilizer or surfactant, and does not contain a dimethyl polyether-polysiloxane amount that exceeds the mass of the aforementioned component (A), and particularly preferably essentially does not contain a dimethyl polysiloxane. Dimethyl polysiloxane is a hydrophobic silicone oil agent, and in a case where the dimethyl polysiloxane is included in the dispersing medium of the composition of the present invention, a function as a foam stabilizer or surfactant may be adversely affected. Note that the polyether-polysiloxane block copolymer composition of the present invention may contain organosilicon compounds other than dimethyl polysiloxane such as other polyether-modified silicones and other organic modified silicones, silanes, and the like within a range that does not impair the technical effects of the present invention. In this case, the amount of organosilicon compounds other than the dimethyl polysiloxanes is preferably within a range that does not exceed the same amount as the mass of the aforementioned component (A), and from the perspective of function as a foam stabilizer or surfactant, the polyether-polysiloxane block copolymer composition may be a composition that essentially does not contain another organosilicon compound.

Component (C)

The polyether-polysiloxane block copolymer may further contain (C) at least one type of polyalkylene glycol or derivative thereof, which is a liquid at 25° C., where one terminal hydroxyl group may be substituted by a hydrocarbon group with 1 to 8 carbon atoms selected from alkyl, aralkyl, and aryl groups, and the repeating number of oxyalkylene units with 2 to 4 carbon atoms is within a range of 4 to 50. Using component (C) has advantages where the viscosity or the like of the composition of the present invention can be adjusted, and convenience during use and handling workability (handling) can be improved, without adversely affecting a function as a foam stabilizer or surfactant Furthermore, component (C) has an advantage where the component can be used by adding to the polyether-polysiloxane block copolymer composition in order to adjust the hydroxyl group value in a polyurethane foam-forming composition, in other words, in order to control crosslinking density, strength, and other various physical properties of polyurethane foam.

More specifically, component (C) may be one type or more selected from the following component (C1) and component (C2), or may be a mixture of component (C1) and component (C2), based on the presence or absence of a substitution of one terminal hydroxyl group.

Component (C1) is a polyoxyalkylene glycol having a hydroxyl group on both terminals of a molecular chain, where the repeating number of oxyalkylene units with 2 to 4 carbon atoms (in other words, degree of polymerization of a polyoxyalkylene portion) is 4 to 50. The compound is preferably a liquid, and typical examples include polypropylene glycols having various degrees of polymerization. The repeating number of oxyalkylene units with 2 to 4 carbon atoms is preferably 4 to 35, and particularly preferably within a range of 6 to 20.

Component (C2) is a polyalkylene glycol derivative containing an oxyalkylene unit (however, the oxyalkylene is arbitrarily selected from oxyalkylenes with 2 to 4 carbon atoms) where one terminal hydroxyl group a substituted by a hydrocarbon group with 1 to 8 carbon atoms selected from alkyl, aralkyl, and aryl groups, the other terminal is an unsubstituted hydroxyl group, and a center portion of the molecular chain has a repeating number of 4 to 50. The compound is preferably a liquid, and typical examples include monobutyl ethers of polypropylene glycols having various degrees of polymerization, and the like. The repeating number of oxyalkylene units with 2 to 4 carbon atoms is preferably 4 to 35, and particularly preferably within a range of 6 to 20.

The amount of component (C) in the present invention composition is within a range of 10 to 300 parts by mass, and may be within a range of 15 to 200 parts by mass, with regard to a total of 100 parts by mass of component (A) and component (B). At this time, the viscosity at 25° C. of the entire composition is preferably within a range of 100 to 35000 mm$^2$/s, and the amount of component (C), component (A), and component (B) can be adjusted in order to satisfy the aforementioned viscosity range, or based on the physical properties of a required polyurethane foam.

The polyether-polysiloxane block copolymer composition of the present invention may contain water soluble alcohols other than component (B) and component (C), so long as the technical effects thereof are not impaired. Examples of the water soluble alcohols include ethanols, ethylene glycols, propylene glycols, butylene glycols, dipropylene glycols, tripropylene glycols, diethylene glycols, isopropanols, and other alcohols or glycols with 1 to 4 carbon atoms.

The polyether-polysiloxane block copolymer composition of the present invention is gradually oxidized and deteriorated by oxygen in air. In order to prevent this, phenols, hydroquinones, benzoquinones, aromatic amines, vitamins, or other antioxidants can be and is preferably inserted to increase the oxidation stability. For example, BHT (2,6-di-t-butyl-p-cresol), vitamin C, vitamin E, and the like can be used as the antioxidant. At this time, the mass of the added amount of used antioxidants is within a range of 10 to 1000 ppm, and preferably 50 to 500 ppm with regard to the polyether-polysiloxane block copolymer.

Reduction of Low Molecular Siloxane

For the polyether-polysiloxane block copolymer composition of the present invention, the amount of low molecular siloxane with 20 or less silicon atoms is preferably 5000 ppm (weight) or less, and particularly preferably 2000 ppm (weight) or less. When the value exceeds 5000 ppm, in particular, using the polyether-polysiloxane block copolymer composition of the present invention as a foam stabilizer of polyurethane foam or the like may contaminate of member around a location where the polyurethane foam is installed, or may cause contact failure of an electrical/electronic device. Examples of the low molecular siloxane include cyclic and straight chain siloxanes such as cyclic dimethyl siloxanes as expressed by formula: [(CH3)2SiO]n (where n represents an integer from 3 to 10), and straight chain dimethyl siloxane oligomers as expressed by formula: CH3[(CH3)2SiO]mSi(CH3)3 (where m represents an integer from 1 to 10), as well as siloxanes where a portion of the methyl groups is substituted by another organic group. Specific examples of the low molecular siloxane include octamethyl tetrasiloxanes, decamethyl pentacyclosiloxanes, and dimethyl siloxane oligomers blocked by a trimethyl siloxane group on both terminals. The amount of the low molecular siloxane can be measured, for example, by adding an organic solvent to the present invention composition, solvent extracting the low molecular siloxane, and then analyzing the extract using a gas chromatography analyzing device.

Reduction of the low molecular siloxane is manufactured, for example, by removing the low molecular siloxane from the present invention composition obtained by a method described in JP 2000-313730A or the like. There are many methods for removing the low molecular siloxane. Examples include: a method of performing treatment under high temperature and high vacuum while an inert gas such as argon gas, nitrogen gas, or the like is blown into a silicone-based foam stabilizer a small amount at a time; a method of thinning the present invention composition and then stripping under a heating condition of 50 to 130° C. under a reduced pressure of 0.5 mm or less; and a method of adding to the silicone-based foam stabilizer an organic solvent that dissolves low molecular siloxane but does not dissolve high molecular siloxane, such as methanol, ethanol, or other organic solvent to extracting to remove the low molecular siloxane. Herein, if thermal decomposition is a concern in treatment at a high temperature, an antioxidant can be added in advance to an extent that does not affect the present invention composition.

Manufacturing Method

For the polyether-polysiloxane block copolymer composition of the present invention, the organopolysiloxane containing a SiH group on both terminals as expressed by General Formula (2) and the polyether containing a methallyl group on both terminals of a molecular chain, as expressed by General Formula (3) are preferably hydrosilylation reacted to obtain a polyether-polysiloxane block copolymer which is component (A). At this time, a step of initiating or promoting a hydrosilylation reaction may be performed without a solvent, in the presence of the monool organic compound which is the aforementioned component (B), or in the presence of a volatile organic solvent (B') that is different from the aforementioned component (B). Note that in a case where a hydrosilylation reaction for obtaining component (A) is initiated or promoted without a solvent/in the presence of a volatile organic solvent (B') that is different from component (B), a step of adding component (B) is further required.

A hydrosilylation reaction catalyst is not limited to a specific catalyst, so long as a hydrosilylation reaction can be promoted. Many metals and compounds are known thus far as hydrosilylation reaction catalysts, which can be appropriately selected and used in the present invention. Specific examples of the hydrosilylation reaction catalyst can include fine particulate platinum adsorbed on silica fine powder or a carbon powder carrier, chloroplatinic acids, alcohol-modified chloroplatinic acids, olefin complexes of a chloroplatinic acid, coordinate compounds of a chloroplatinic acid and vinyl siloxane, platinum black, palladium, and rhodium catalysts.

The used amount of the hydrosilylation reaction catalyst is an effective amount, and is not particularly limited so long as the amount promotes a polymerization reaction of the polyether-polysiloxane block copolymer composition of the present invention. Specifically, the metal atoms in the catalyst is an amount within a range of 0.01 to 1,000 ppm by mass units, and platinum metal atoms are preferably within a range of 0.1 to 500 ppm, with regard to the total amount (entire body set as 100 mass %) of organopolysiloxane containing a SiH group on both terminals as expressed by General Formula (2) and polyether containing a methallyl group on both terminals in a molecular chain as expressed by General Formula (3). This is because when the amount of hydrosilylation reaction catalysts is less than the lower limit of the aforementioned range, a copolymerization reaction may be insufficient, and when the amount exceeds the upper limit of the aforementioned range, coloring or the like and transparency of the obtained present invention composition may be adversely affect in addition to being uneconomical.

As described above, from the perspective of use as a foam stabilizer and stability of the copolymer, component (A) of the present invention is preferably a polyether-polysiloxane block copolymer where one terminal or both terminals is blocked by a functional group including a polyether portion, and a polyether raw material containing a methallyl group or the like on both terminals is preferably added to an organopolysiloxane containing a SiH group on both terminals such that the substance amount of methallyl groups in the polyether raw material is an equal or slightly excess amount with regard to the silicon-bonded hydrogen atoms in the organopolysiloxane containing a SiH group on both terminals, and then carrying out hydrosilylation reaction. Specifically, the reaction is preferably performed at an amount where the ratio (molar ratio) of the substance amount of methallyl groups ($R^{vi}$) in the polyether raw material and silicon-bonded hydrogen atoms (Si—H) in the organopolysiloxane containing a SiH group on both terminals is $[R^{vi}]/[Si—H]=1.0$ to $1.50$, and preferably $1.0$ to $1.20$.

The hydrosilylation reaction conditions can be arbitrarily selected based on the raw material and the presence or absence of a solvent described later, but the composition can be obtained by adding a small amount of an antioxidant such as tocopherol (vitamin E), BHT (butylated hydroxytoluene), or the like, and then heating and stirring at room temperature to 200° C., and preferably 70 to 150° C. under an inert gas atmosphere such as nitrogen or the like. Note that the antioxidant may be added after hydrosilylation is completed. The reaction time can be selected based on the reaction scale, amount of catalyst used, and reaction temperature, and is generally within a range of several minutes to several hours. Furthermore, the reaction may be performed under reduced pressure in order to improve quality or the like, and for example, the reaction conditions proposed in JP 11-116670 A can be applied without particularly limitation.

Note that the end point of the hydrosilylation reaction can be confirmed by the disappearance of Si—H bond absorption by infrared spectroscopy (IR), or the absence of hydrogen gas generation by an alkali decomposition gas. Note that the silicon-bonded hydrogen atoms (Si—H) in the organopolysiloxane containing a SiH group on both terminals which is a reaction raw material can be analyzed by the same method, and therefore, the amount of hydrogen gas generation can be specified.

Alkali Decomposition Gas Generation Method: Method of reacting at room temperature a 28.5 mass % caustic potash ethanol/water mixed solution with a solution where a sample is dissolved in toluene or IPA, collecting the generated hydrogen gas in a collection tube, and then measuring the volume thereof.

Furthermore, potassium acetate, potassium propionate, other carboxylic acid alkali metal salt, or the like can be added in order to suppress a side reaction or the like, so long as the technical effects of the polyether-polysiloxane block copolymer composition of the present invention are not impaired.

Optional Purification/Low Bromination Treatment

Furthermore, in a case where purification or low bromination of a crude product is required based on the application of the polyether-polysiloxane block copolymer of the present invention, a known purification method in the related art such as hydrogenation, contact with an acidic substance, removal of generated aldehydes, or the like may be used. These methods can be selected without particular limitation from purification method 1 and purification method 2 proposed in paragraph 0031 of JP 2007-186557 A and the like, a method for reducing odor proposed in JP 2000-327785 A and the like, a treatment method using an acidic inorganic salt proposed in JP 2011-116902 A by the present applicant, and the like. In particular, by using the purification methods, the amount of harmful aldehydes generated over time is very low even if the composition is added to polyurethane foam. Thus, the composition has advantages where use as a cosmetic raw material is further improved in addition to being useful as a foam stabilizer of polyurethane foam applied in building materials, the automotive industry (such as automotive interior material), beds, sofas, and other furniture, bedding, clothing, and the like.

Hydrosilylation Reaction in Inorganic Solvent→Addition of Component (B)

The polyether-polysiloxane block copolymer composition of the present invention can be preferably manufactured by a manufacturing method at least including a step of initiating hydrosilylation between the organopolysiloxane containing a SiH group on both terminals as expressed by General Formula (2) and the polyether containing a methallyl group ($R^{vi}$) on both terminals of a molecular chain as expressed by General Formula (3) in the essential absence a solvent, and a step of diluting or promoting a reaction by adding the monool organic compound which is the aforementioned component (B) after the reaction is completed or during the reaction. Diluting can be performed by adding component (B) after completing the reaction in the absence a solvent, or the reaction can be completed by adding component (B) from a stage partway through a reaction in the absence of a solvent. In principle, the present manufacturing method does not require a stripping step. Furthermore, the polyether-polysiloxane block copolymer of the present invention has excellent performance as a foam stabilizer, and therefore, foam stabilization is likely to occur. Therefore, when performing a reaction in the presence of a solvent such as toluene and reduced pressure removal (stripping) is performed in order to remove the toluene or the like, the generated foam will not breakdown and will cover up to an upper portion of a reaction tank, and therefore the cycle time on industrial production may increase, which is disadvantageous, but by initiating the reaction in the absence of a solvent, there are cases where industrial production problems can be resolved. Note that the reaction is initiated in the absence a solvent, and after the reaction has progressed to a certain point, the monool organic compound which is the aforementioned component (B) is added, and therefore, increase in viscosity due copolymerization is suppressed, and thus stirring efficiency and reactivity can be improved. Note that a method described in JP 01-101333 A or the like may be used as a method of synthesizing the polyether-polysiloxane block copolymer in the absence a solvent.

Hydrosilylation Reaction in the Presence of Component (B)

The polyether-polysiloxane block copolymer composition of the present invention can be preferably manufactured by a manufacturing method at least including a step of initiating or promoting hydrosilylation between the organopolysiloxane containing a SiH group on both terminals as expressed by General Formula (2) and the polyether containing a methallyl group on both terminals of a molecular chain as expressed by General Formula (3) in the presence of the monool organic compound which is the aforementioned component (B). In the present manufacturing method, a solvent or diluting agent other than component (B) can be simultaneously present, but in a case where they are not, a stripping step is not required. On the other hand, if a solvent or diluting agent other than component (B) is simultaneously present, a stripping step is present only when the solvent or diluting agent needs to be removed after the reaction is completed. The method almost has no problems with foaming in the aforementioned manufacturing step and deterioration of industrial production efficiency, does not require an additional step such as solvent exchange or the like if a solvent other than component (B) is not used, has excellent stirring efficiency and reaction efficiency due to suppressed reaction viscosity of the obtained composition and reaction initiation, and can significantly improve the quality and function of the obtained polyether-polysiloxane block copolymer composition as a surfactant or foam stabilizer.

Hydrosilylation Reaction in the Presence of Different Volatile Organic Solvent (B')→Solvent Exchange to Component (B)

The polyether-polysiloxane block copolymer composition of the present invention can be preferably manufactured by a manufacturing method at least including: a step of initiating or promoting hydrosilylation between the organopolysiloxane containing a SiH group on both terminals as expressed by General Formula (2) and the polyether containing a methallyl group on both terminals of a molecular chain as expressed by General Formula (3) in the presence of a volatile organic solvent (B') that is different from the aforementioned component (B); and a step of performing solvent exchange of the volatile organic solvent (B') that is different from component (B) with the monool organic compound which is the aforementioned component (B).

The volatile organic solvent (B') used in the method is not particularly limited so long as the solvent is different from the aforementioned component (B) and has a lower boiling point than component (B), and a solvent with a boiling point of 60° C. to 200° C. is preferably used. Examples include ethanols, i-propyl alcohols, 1-butanols, t-butyl alcohols, cyclohexanols, cyclohexanones, methyl ethyl ketones, methyl isobutyl ketones, isododecanes, toluenes, xylenes, mesitylenes, 1,4-dioxanes, dibutyl ethers, anisoles, 4-methyl anisoles, ethyl benzenes, ethoxy benzenes, ethylene glycol dimethyl ethers, ethylene glycol diethyl ethers, 2-methoxy ethanols (ethylene glycol monomethyl ethers), diethylene glycol dimethyl ethers, diethylene glycol monomethyl ethers, 1-methoxy-2-propyl acetates, 1-ethoxy-2-propyl acetates, octamethyl cyclotetrasiloxanes, hexamethyl disiloxanes, and other non-halogen solvents, trifluoromethyl benzenes, 1,2-bis (trifluoromethyl) benzenes, 1,3-bis (trifluoromethyl) benzenes, 1,4-bis (trifluoromethyl) benzenes, trifluoromethyl chlorobenzenes, trifluoromethyl fluorobenzenes, hydrofluoroethers, and other halogen solvents. The volatile organic solvent can be used independently or as a mixture of two or more types thereof.

After completing the synthesis reaction of the polyether-polysiloxane block copolymer of the present invention, the volatile organic solvent (B') is removed by stripping or the like, and then solvent exchange with the monool organic compound which is component (B) can be performed. Note that in the hydrosilylation reaction step using the volatile organic solvent (B') such as toluene or the like, foam generated from the polymerized polyether-polysiloxane block copolymer during stirring may be stabilized, and therefore, in the industrial production process, the degree of pressure reduction, heating temperature, and stirring rate during stripping is preferably appropriately controlled. Increase in manufacturing time due to foam generation during stripping is suppressed, and therefore, a reaction can be initiated from a condition where the pressure is reduced in advance to a certain degree.

Herein, the method used in the solvent exchange is not particularly limited, but in the hydrosilylation reaction step using the volatile organic solvent (B') such as toluene of the like for example, the organic solvent may be removed using a rotary evaporating device or the like, and then solvent exchange with the monool organic compound which is component (B) may be performed in accordance with a method described in JP 08-156143 A.

As described above, a liquid polyether-polysiloxane block copolymer according to the present invention can be manufactured by a plurality of methods. However, a process that essentially does not include a stripping step is preferable from the perspective of avoiding foaming problems during the manufacturing step and making the production step more efficient. In particular, a process of initiating the hydrosilylation reaction in the presence of component (B) is preferable.

Use of Present Invention Composition: Surfactant or the Like

The polyether-polysiloxane block copolymer composition of the present invention has a polyether site and a silicone site with mutually different hydrophilicity in a molecule, and therefore can be used without particularly limitation in known applications in the related art of a polyether-polysiloxane block copolymer, and can be used without particularly limitation in surfactants, foam stabilizers, fiber lubricity imparting agents, reactive raw materials of other polymeric materials, and the like. The polyether-polysiloxane block copolymer composition of the present invention is useful as an industrial or cosmetic surfactant, where the formulation destination is paint, coating agents, construction materials, cosmetics, hydrophilicity imparting agents, surface treating agents, foamable resin compositions, and the like, and is not particularly limited. Furthermore, based on a function as a surfactant, the composition is particularly useful as a paint additive, emulsifier, solubilizer, foam stabilizer for polyurethane foam, or cosmetic raw material.

Use of Present Invention Composition: Foam Stabilizer

The polyether-polysiloxane block copolymer composition of the present invention can be preferably used as surfactant for foam control or foam stabilizing, and particularly a foam stabilizer during manufacturing of a foamable resin, and particularly polyurethane foam. In particular, the composition according to the present invention has advantages where not only foam stabilization but the open cell ratio can be controlled, homogeneity and stability of a premixed solution are excellent, compatibility with various components in an emulsion composition for foam forming is excellent, and foam retaining properties in microcellular applications is excellent.

Furthermore, for the polyether-polysiloxane block copolymer composition of the present invention, the molar ratio between the organopolysiloxane containing a SiH group on both terminals as expressed by General Formula (2) and the polyether containing an alkenyl group on both terminals as expressed by General Formula (3) is adjusted to enable design of the average molecular weight of the copolymer. Furthermore, surface activating performance, affinity to a urethane foam system, and the like can be controlled based on the EO % or size of a polyether portion and introduction of a hydroxyl group or hydrophobic group to a copolymer terminal portion. Therefore, the modified silicone can demonstrate an excellent effect as a surfactant for foam control or foam stabilizing in all polyurethane foam formulations other than high resilience foam, where the molecular weight of a foam stabilizer is required to be designed very small.

Furthermore, the polyether-polysiloxane block copolymer composition of the present invention has a wide selection of manufacturing steps, and problems with controlling foam generated during a manufacturing step can easily be resolved or the problems can easily be resolved even if a desired copolymer is designed, and therefore, productivity is excellent, manufacturing problems directly linked to industrial production cost and application problems are comprehensively resolved, foam stabilizers containing the new polyether-polysiloxane block copolymer composition can sufficiently spread in the market, and can be used as a high performance raw material.

Polyurethane Foam-Forming Composition

The foam stabilizer is used in manufacturing polyurethane foam. Therefore, so long as the polyurethane foam-forming composition of the present invention contains the polyether-polysiloxane block copolymer composition of the present invention which is the aforementioned foam stabilizer, the type, properties, and type of applied formulation are not particularly limited.

Type of Foam

In general, polyurethane foam includes hard polyurethane foam and soft polyurethane foam, which are specifically classified into soft urethane foam, high resilience urethane foam, hard urethane foam, and special foam. The polyurethane foam-forming composition of the present invention has excellent handling workability (handling) and the like, and therefore demonstrates excellent effects as a foam stabilizer in all polyurethane foam formulations other than high resilience foam generally required in foam stabilizers with a low molecular weight.

Soft urethane foam is widely used as a cushion material for sofas or beds and sheets for automobiles and the like. The viscosity of a soft slab foam raw material system is relatively low and has a high foam expansion ratio, and therefore, stabilization of a cell membrane during cell growth is a major key. A foam stabilizer with a relatively high molecular weight (polyether-modified silicone) is well suited for this system. Furthermore, compatibility with 3000# polyol is ensured, and therefore, a type where polyether with a relatively high propylene oxide ratio is graft modified is widely used. A type where a modified polyether terminal is uncapped (hydroxyl group) has an effect of strengthening cell foaming properties, and therefore, types where the polyether terminal is capped (often methoxy capped) are widely used, which aids in simplifying cell membrane communication. The polyether-polysiloxane block copolymer composition of the present invention is a foam stabilizer containing a surfactant with a relatively high molecular weight and a specific monool organic compound, and can be suitably used in the system. On the other hand, a soft hot mold formulation contains a urethane raw liquid system that is considerably close to a soft slab formulation, and has high reactivity and is in a packed condition in a mold, and therefore, ensuring high air permeability is important. The polyether-polysiloxane block copolymer composition of the present invention can achieve high air permeability, and can be used in the formulation.

A flame retardant foam-compatible type foam stabilizer is defined as a type that can reduced the number of flame retardant additives in the formulation and a type that reduces adverse effects on foam physical properties caused by adding a flame retardant. However, a silicone foam stabilizer is generally positioned as a combustion improver. This is because when the foam is melted in a liquid form by heat, the silicone foam stabilizer gathers on a liquid surface due to a surface activating effect, which prevents carbonization. Therefore, for a flame retardant foam, a foam stabilizer with a relatively low silicone content rate and low foam stabilizing activity. The polyether-polysiloxane block copolymer composition of the present invention may be used as a flame retardant foam-compatible type foam stabilizer.

High resilience foam (HR foam) is mainly molded foam of an automotive seat or the like, and therefore requires improved moldability and air permeability. The HR foam has high system viscosity and high reactivity, and therefore, stabilization of a cell membrane is relatively simple, but connecting does not advance, and thus problems such as cracking due to gas accumulated inside the foam, shrinking after demolding, and the like needs to be prevented. Therefore, foam stabilizers with cell opening properties and very weak foam stabilizing capacity are generally widely used. This type is designed with a very low foam stabilizer molecular weight, and initial raw material component emulsification is achieved, but has a feature where the retention capacity of the cell membrane is very weak.

Furthermore, in the system, a dimethyl polysiloxane with a relatively low molecular weight where polyether is not modified is also applied. When combined with polyether-modified silicone, these substances can adjust the strength of the cell openability/foam stabilizing capacity by optimizing the molecular weight distribution while functioning as a foam stabilizing auxiliary agent providing stabilized foam stabilizing activity (moldability).

A type with a stronger foam stabilizing capacity and fine celling is suitable for TDI based formulations which require high activity, but on the other hand, a type providing weaker foam stabilizing capacity, favorable crushing properties, and high air permeability is suitable for MDI based formulations with a relatively strong foaming properties. Furthermore, by a type with strong foam stabilizing capacity and a type with weak foam stabilizing capacity, adjusting the cell size and air permeability is widely applied in production, and is a technique unique to the system.

However, polyether-modified silicone with a very low molecular weight and dimethyl polysiloxane with a low molecular weight, generally used in high resilience foam applications have a problem of a narrow processing range (degree of freedom of foam formulation or narrowness of permissible range), and in order to resolve this problem, an appropriate amount of the polyether-polysiloxane block copolymer composition of the present invention can be used in combination.

The hard urethane foam is lightweight, has excellent heat insulating properties, and high productivity, and therefore is widely used as a heat insulating material for refrigerators and the like and building materials. In order to improve heat insulating properties of the hard urethane foam, making the cell size as fine as possible is important. The number of cells in the finally obtained foam and the number of entrapped gases dispersed during initial urethane foaming liquid stirring essentially match. Therefore, a foam stabilizer that enhances the emulsifying capacity is optimal in initial stirring. On the other hand, as the cells become finer, the foam is prone to shrinking. In this case, a type with relatively low foam stabilizing activity is formulated, and the cell size is increased, and therefore, an effect of preventing shrinking is increased. Note that polyisocyanate foam with excellent flame retardance is classified as a hard urethane foam.

In the hard urethane foam, HCFC141b used as a foaming agent in the past is regulated from the perspective of global environment, and a HFC compound which is a substitute product thereof is moving towards regulations in the near future. An effect provided on the urethane formulation by the foaming agent is large, and an optimal foam stabilizer needs to be selected based on the type thereof.

In a water formulation and a HFC formulation with a high number of hydrogens, initial emulsifying capacity is reduced as compared to HCFC-141b formulations which had favorable urethane compatibility with a urethane raw material system. Therefore, by formulating a foam stabilizer with high foam stabilizing activity, favorable cells can be expected to be obtained. Furthermore, premixed compatibility may be required in a cyclopentane formulation from the perspective of storage stability. In this case, compatibility with a base polyol is important, and a type with a high E0 (ethylene oxide) ratio of modified polyether and with a hydroxyl group (—OH) terminal exhibits relatively favorable compatibility.

The polyether-polysiloxane block copolymer composition of the present invention is a foam stabilizer containing a specific monool organic compound and a surfactant with a relatively high molecular weight, which is suitable for the system, and can adjust the emulsifying properties, molecular weight, and terminal functional group as desired, and therefore can be added without particular limitation in a hard urethane foam and water formulation.

Examples of special foam include: semi-hard foam which is an intermediate material of soft foam and hard foam; low resilience foam derived from soft foam but with a unique application and position due to a unique viscoelastic behavior; high density foam called integral skin used for shoe soles and the like; microcellular foam manufactured by a mechanical foaming (mechanical flossing) method; and the like.

Furthermore, for raw material polyols of urethane foam, foam manufactured using polyester polyols and not general polyether polyols is referred to as ester foam, and has a classification based on foam properties as described above.

Heat insulating properties are important in many applications of hard foam, and therefore, a closed cell type foam with a high foaming rate is normally required, but emphasis is placed on dimensional stability for some applications, and selection of a surfactant or formulation of a foam composition are devised so as to partially open cells. Conversely, with general soft foam, at the moment that formation of a polyurethane structure by a reaction between a polyol and isocyanate and reaction heat and foam rise due to a foaming agent stop due to a structure increasing in strength based on the progress of crosslinking, a formulation is designed such that all cell (foam) membranes in the structure break (open) and are connected (continuously ventilate).

Formulation of low resilience foam is similar to general soft foam formulation, but improvisations are adopted to incorporate a structural element having viscoelasticity in raw material polyol. Therefore, the degree of difficulty of cell connection increases, and the importance of a surfactant having a high open cell effect increases. Furthermore, even in a field of a high density microcellular foam by mechanical foaming method or HR, various applications are produced by controlling the open cell ratio.

The polyether-polysiloxane block copolymer composition of the present invention is a foam stabilizer that is suitable for controlling the open cell ratio, is not only the foam stabilizing agent and can control the open cell ratio, even in fields such as high-density microcellular foam by a mechanical foaming method, other hard foams or soft foams, and the like.

The polyurethane foam-forming composition of the present invention preferably contains:
a polyurethane foam-forming composition, comprising:
(a) a polyol;
(b) a polyisocyanate;
(c) a catalyst;
(d) a foam stabilizer containing the polyether-polysiloxane block copolymer composition according to any one of claims 1 to 7; and (e) optionally, at least one added component selected from a group consisting of foam stabilizers other than component (d), foaming agents, diluting agents, chain extenders, crosslinking agents, water, nonaqueous foaming agents, fillers, reinforcing agents, pigments, dyes, coloring agents, flame retardants, antioxidants, anti-ozone agents, UV stabilizers, antistatic agents, disinfectants, and antibacterial agents.

The components are outlined below.

(a) Polyol

Examples of polyols include polyether polyols, polyester polyols, and the like. The polyether polyol is obtained by adding an alkylene oxide to a polyhydric alcohol, saccharide, phenol, phenol derivative, aromatic amine, or the like, and examples include polyether polyols obtained adding an alkylene oxide to one type or two or more types of a glycerin, propylene glycol, dipropylene glycol, ethylene glycol, diethylene glycol, trimethylol propane, pentaerythritol, sucrose, sorbital, novolak, nonylphenol, bisphenol A, bisphenol F, tolylenediamine, diphenylmethane diamine, or the like. Examples of the polyester polyols include polyols having a hydroxyl group on a terminal, manufactured by condensation polymerization between an adipic acid, phthalic acid, succinic acid, or other polyfunctional carboxylic acid, and a glycerin, propylene glycol, dipropylene glycol, ethylene glycol, diethylene glycol, trimethylol propane, pentaerythritol, or other polyfunctional hydroxyl compound. One type of polyol may be used independently or two or more types may be used in combination.

A polyol preferred in preparing the polyurethane foam of the present invention has 2 to 8 hydroxyl groups per molecule, and has a number average molecular weight of 200 to 10000, and preferably 500 to 7500. Examples of useful polyether polyols include Vorano1220-028, Vorano1220-094, Vorano1225, Vorano1270, Vorano1490, and Vorano1800 (Dow Chemical Company), Arco111-34 (Bayer Material Science), and the like.

Polylols such as polyether polyols and polyester polyols have a number of hydroxyls (hydroxyl value) that is normally within a range of approximately 15 to approximately 700. The number of hydroxyls is preferably approximately 20 to 60 for soft foam, approximately 100 to 300 for semi-soft (or semi-hard) foam, and approximately 250 to 700 for hard foam. For soft foam, the preferable functional value, in other words, the number of average hydroxyl groups per polyol molecules of a polyol is approximately 2 to 4, and most preferably approximately 2.3 to approximately 3.5. For hard foam, the preferable functional value is approximately 2 to approximately 8, and most preferably approximately 3 to approximately 5.

The foam stabilizer of the present invention can be used as a foam stabilizer suitable for most polyurethane foam. The added amount thereof is within a range where the polyether-polysiloxane block copolymer (A) in the polyether-polysiloxane block copolymer composition is 0.5 to 8.0 parts by mass, preferably within a range of 0.5 to 4.0 parts by mass, and more preferably 1.0 to 2.0 parts by mass with regard to 100 parts by mass of polyols.

(b) Polyisocyanate

Known polyisocyanates in the related art can all be used as an organic polyisocyanate, but the most general polyisocyanates include tolylene diisocyanates (hereinafter, referred to as "TDI") and diphenyl methane diisocyanates (hereinafter, referred to as "MDI"). TDI of a mixture of isomers, in other words, 100% 2,4-isomer products, 2,4-isomer/2,6-isomer=80/20, 65/35 (mass ratio), and the like can be used as well as crude TDI containing a polyfunctional tar. A polymeric MDI containing a polynuclear body with 3 or more nuclei can be used as the MDI in addition to pure products primarily containing 4,4'-diphenyl methane diisocyanate.

Of the isocyanate compounds, MDI is normally used in manufacturing hard polyurethane foam, and TDI is normally used in manufacturing soft polyurethane foam.

An isocyanate prepolymer of MDI is prepared by reacting the MDI with a polyol, or by combining a modified compound such as a uretonimine-modified compound with the aforementioned MDI derivatives at an arbitrary ratio. Similarly, a preferable product is toluene diisocyanate (TDI), including 2,4- and 2,6-isomers thereof, TDI isocyanate prepolymers manufactured by reacting TDI with a polymer, and prepolymers made by combining these with other aromatic or aliphatic polyisocyanates or uretonimine modified polyisocyanates. A mixture of polyisocyanates naturally falls within the scope of the present invention.

The added amount of the polyisocyanate with regard to the amount of other materials in the formulation is expressed as "isocyanate index". The "isocyanate index" is a value obtained by dividing the actual used amount of polyisocyanate by the stoichiometric amount of polyisocyanate required for reacting with a fully active hydrogen in the reaction mixture, and then multiplying by 100. The isocyanate index in the polyurethane foam-forming composition using the method of the present invention is generally 60 to 140. In general, the isocyanate index is generally 85 to 120 in soft TDI foam, normally 90 to 105 in molded TDI foam which is a high resilience (HR) foam, usually 70 to 90 in molded MDI foam, and generally 90 to 130 in hard MDI foam. Several examples of polyisocyanurate hard foam are manufactured with a high index of 250 to 400.

(c) Catalyst

Examples include nickel acetoacetonates, iron acetoacetonates, tin-based catalysts, bismuth-based catalysts, zinc-based catalysts, titanium-based catalysts, aluminum complexes, zirconium complexes, potassium octylates, potassium acetates, sodium acetates, sodium octylates, metal oxide particles having a solid acid point on a surface, triethylenediamines, bis (dimethyl aminoethyl) ethers and other tertiary amine urethane catalysts, imidazole derivatives, carboxylic acid quaternary ammonium salts, delayed tertiary amine catalysts, general tertiary amine catalysts, low emission tertiary amine catalysts, non-emission tertiary amine catalysts, and DABCO (registered trademark) catalysts from Air Products for example.

Of these catalysts, amine-based catalysts are preferable in manufacturing hard polyurethane foam, and amine-based catalysts and tin-based catalysts are preferably used in combination in manufacturing soft polyurethane foam.

(d) Foam Stabilizer Containing Polyether-Polysiloxane Block Copolymer Composition of the Present Invention The polyether-polysiloxane block copolymer composition of the present invention is as described above, but in general, there is a correlation in compatibility between the type of foam resin and silicones containing a polyether portion, which is a foam stabilizer, and when arranging from foam suitable for low molecular weight bodies to foam suitable for high molecular weight bodies, the order is high resilience foam<hard foam<soft foam<microcellular foam.

Furthermore, the structure of the polyether portion also greatly affects the size of the foam and the like, and therefore, techniques exist for increasing the molecular weight distribution of a polyether portion and the like, such as selecting a polyether structure with a high amount of EO if reduced cell size and air permeability are desired, selecting a polyether with a high molecular weight if foam stabilization and retention are desired, widening the processing range, using a plurality of polyethers with different molecular weights or structures in raw material in order to have compatibility with a wide range of applications and formulations, and the like, which can also be applied in the polyether-polysiloxane block copolymer composition of the present invention. Furthermore, a polyol which is one primary raw material of polyurethane has a PPG structure portion, and therefore, a PO (propyleneoxy) chain is often preferably also included in the polyether portion in the polyether-modified silicone from the perspective of compatibility in a foam formulation.

These requirements are different based on the type of polyurethane foam where the polyether-polysiloxane block copolymer composition of the present invention is added, but the surface activating performance, affinity to the urethane foam system, or the like can be controlled based on appropriately adjusting the type, reaction ratio, or the like of organopolysiloxane containing a SiH group on both terminals as expressed by General Formula (2) or polyether containing an alkenyl group on both terminals as expressed by General Formula (3), or based on the EO/PO % or size of the polyether portion and introducing a hydroxyl group or hydrophobic group to the copolymer terminal portion, and therefore, an advantage is provided where a suitable foam stabilizer can be freely designed as desired.

(e) Optional Components

Particularly, important components of the optional components in the polyurethane foam-forming composition are water and a nonaqueous foaming agent. Water functions as a chemical foaming agent by reacting with polyisocyanate to generate carbon dioxide gas. In addition thereto, one or more physical and/or chemical nonaqueous foaming agent can be included in the reaction mixture. Furthermore, water may not be used based on the formulation. The foaming agents can include HFC-245fa, HFC-134a, and other hydrofluorocarbons, HFO, HCFO, and other hydrofluoroolefins, iso-, cyclo-, and n-pentanes, and other hydrocarbons with a low boiling point, supercritical carbon dioxide gases, formic acids, and the like.

Water is often used as a reactive foaming agent in both soft foam and hard foam. When manufacturing soft foam, water can generally be used at a concentration of 2 to 6.5 parts per 100 parts of polyols for example, and is typically 3.5 to 5.5 parts. Of the high resilience (HR) foam, the amount of water in the TDI molded foam is typically 3 to 4.5 parts for example. In the MDI molded foam, the amount of water is typically 2.5 to 5 parts for example. On the other hand, the amount of water in hard foam is 0.5 to 5 parts, and typically 0.5 to 1 parts, for example. A physical foaming agent such as foaming agents with a volatile hydrocarbon, halogenated hydrocarbon, or other non-reactive gas as a base can also be used in manufacturing the polyurethane foam according to the present invention. Manufactured hard heat insulating foam foams using volatile hydrocarbon or halogenated hydrocarbon at a substantial ratio, and preferable foaming agents include a hydrochlorofluorocarbon (HCFC) and pentane or cyclopentane, which are volatile hydrocarbons. A hydrofluoroolefin (HFO, HCFO) can also be used. When manufacturing a soft slab foam, water is the primary foaming agent, but another foaming agent can also be used as an auxiliary foaming agent. In the soft slab foam, a preferable auxiliary foaming agent includes carbon dioxides and dichloromethane. The high resilience (HR) foam generally does not use an inert auxiliary foaming agent, and in any case, has a lower added amount of auxiliary foaming agents than the slab foam. However, in several molding technology, use of carbon dioxide is most important. The amount of foaming agent differs based on the desired foam density and foam hardness. The amount when using a hydrocarbon foaming agent is a trace amount or 50 parts per 100 parts of polyols for example, and CO2 is approximately 1 to approximately 10% for example.

However, particularly in microcellular applications, hardness is too low, dimensional accuracy required in final products are difficult to achieve, and tensile strength, wear resistance, and other mechanical strength are insufficient in polyurethane foam by chemical foaming using water, hydrofluorocarbons, hydrocarbons with a low boiling pint, and the like as foaming agents, and therefore, high density foam by mechanical foaming is normally manufactured. In other words, air, nitrogen gas, or the like entrapped by mechanical stirring herein primarily configures the core of an air bubble.

Herein, the polyol a), polyisocyanate b), catalyst c), polyether-polysiloxane block copolymer composition d) of the present invention, and water, nonaqueous foaming agent, and other components which are optional components e), which can be included in the polyurethane foam-forming composition can be changed over a wide range as described below, for example. The reason for allowing a wide range is because the formulation of the polyurethane foam-forming composition needs to be adjusted based on the required foam properties, applications, foaming forms, devices, and the like.

6 to 85 parts by mass of polyol a), 10 to 80 parts by mass of polyisocyanate b), 0.01 to 5.0 parts by mass of catalyst c), 0.1 to 20 parts by mass of polyether-polysiloxane block copolymer composition of the present invention d), 0 to 6 parts by mass of water as an optional component, and 0 to 45 parts by mass of a nonaqueous foaming agent as an optional component.

Furthermore, the mass of water that can be included in the polyurethane foam-forming composition is preferably within a range of 0 to 10% with regard to the mass of the polyols.

Other optional components e) may include any known component in the related art in the field such as other polymers and/or copolymers, diluting agents, chain extenders, crosslinking agents, fillers, reinforcing agents, pigments, dyes, coloring agents, flame retardants, antioxidants, antiozone agents, UV stabilizers, antistatic agents, disinfectants, and antibacterial agents, within a normal amount range.

For example, the optional component e) can include a polyhydroxyl terminal compound having a molecular weight of 62 to 500 and 2 to 8 hydroxyl groups per molecule, functioning as a crosslinking agent or chain extender. Examples of crosslinking agents having 3 to 8 hydroxyl groups include glycerins, trimethyloylpropanes, pentaerythritols, mannitols, sorbitols, and the like. Examples of useful chain extenders having two hydroxyl groups include dipropylene glycols, tripropylene glycols, propylene glycols, diethylene glycols, triethylene glycols, 1,4-butanediols, ethylene glycols, 2,3-butanediols, 2-methyl-1,3-propanediols, 1,2-propanediols, 1,3-propanediols, neopentyl glycols, and the like. Diethanol amines, monoethanol amines, and the like can also be used.

Optional component e) may further include a filler such as an inorganic filler or filler combination for example. The filler is a filler for physical performance such as density modification, mechanical performance, or sound absorption, or a filler for improving other advantages including flame retardancy, or economics, such as calcium carbonate, for example, including other fillers that reduce the cost of manufacturing foam, aluminum hydroxides, and other flame retardant fillers, barium sulfates, and other high density fillers used for sound absorption, and glass, polymers, and microspheres of other substances that further reduce the foam density. Examples of a filler or reinforcing agent with a high aspect ratio used for modifying the mechanical performance such as foam rigidity or flexibility module include: artificial fibers such as pulverized glass fibers and graphite fibers; natural mineral fibers such as wollastonite; natural plant fibers such as wool or plant fibers such as cotton; artificial plate-shaped fibers such as pulverized glass; and natural mineral plate-shaped fillers such as mica. Any pigment, dye, or coloring agent which may be added is included. Furthermore, when the present invention is added to an organic flame retardant, anti-ozone agent, or antioxidant; or a thermal or thermal-oxygen decomposition inhibitor, UV stabilizer, or foam-forming composition, the present invention is designed to use any other additive that avoids or inhibits heat, light, and/or chemical decomposition of the produce foam. Additives intended for use herein include antistatic agents, disinfectants, antistatic agents, and gas fade inhibitors in the related art and are arbitrary known.

The polyurethane foam obtained from the polyurethane foam-forming composition of the present invention is preferably hard foam, semi-hard foam, soft foam, or microcellular foam.

Various previously known manufacturing processes can be used in the process of manufacturing the polyurethane foam from the polyurethane foam-forming composition of the present invention. For example, for soft foam, polyurethane foam can be manufactured using a one-shot foaming method, a quasi-prepolymer method, and a prepolymer method. General soft foam is normally industrially produced as slab foam. A certain type of slab foam is manufactured by injecting a reactant mixture into a large box (discontinuous method referred to as box foaming), but normal slab stock foam is continuously manufactured by discharging a reaction mixture onto a conveyor with a paper liner. When the foam foams, cures, and exits a foamer as the conveyor advances, the foam is cut into large blocks.

Furthermore, for hard foam, a manufacturing method of dividing more finely is used based on the purpose and application. For example, a method referred to as a "spray foaming" is a method of spray foaming and hardening a polyurethane foam-forming composition at a site such as a construction site or the like. A "lamination board" is primarily used as a heat insulating material for prefabricated buildings, but may also be referred to as a "heat insulating board", "continuous lamination board stock", or the like. When manufacturing the lamination board, a foamed foam-forming composition continuously fed through a roller between surface members mutually facing up and down is cured while flowing to finally obtain a plate-shaped foam with a thickness of approximately 10 cm. An "appliance" is foam exclusively used for heat insulating material for refrigerators, and is produced by a fully automatic process in a factory using an injection molding method. However, in this case, the process ends by injecting, foaming, and curing the foam-forming composition in a metal mold, and the foam is not removed from the metal mold. The formulation characteristics of foam for refrigerators are that water is not used as a foaming agent (due to carbon dioxide gases having a property of easily transferring heat), because an emphasis is placed on heat insulation. "Site injection" is a literal meaning, but is a method that ends by injecting, foaming, and curing the foam-forming composition in a metal mold at the site, and refers to applications other than refrigerators.

With a "microcellular" which is one special foam, a homogenous and fine density foam is manufactured by a mechanical foaming system referred to as mechanical froth system. A so-called foaming agent is not used herein, and air, nitrogen gas, or the like entrapped by mechanical stirring herein primarily configures the core of an air bubble.

Low resilience foam which is a special foam or soft foam is manufactured by a slab or mold method, similar to general soft foam or HR foam. After flowing a mixed stock solution onto a continuous conveyor, and then normally continuously foaming such that a cross section with 1 to 2 m width and 0.2 to 0.6 m height forms a square or semi-cylindrical shape, a slab product is cut into a bread loaf shape with a predetermined length (often 1 to 2 m). The slab product is shipped in this form to a processing establishment, and a product with various shapes can be cut out and processed from the slab product. After injecting and foaming a stock solution in a plastic or metal mold, a molded product is removed from the die and can be molded in large quantities with dimensional accuracy even with complicated shaped products.

Furthermore, a method of manufacturing an individual polyurethane foam can be appropriately selected, but in particular, the polyether-polysiloxane block copolymer composition of the present invention can be suitably used in place of the silicone-based foam stabilizer, silicone surfactant, or silicone copolymer surfactant in the manufacturing method of a polyurethane foam described in the following patent publications or detailed description of the patent publications, and particularly, the examples and the like. Note that the disclosure of the detailed descriptions thereof or examples include disclosures related to a manufacturing device, and a portion of components may be further substituted and manufacturing conditions thereof may be appropriately modified based on changing viscosity or the like, by normal design modifications of a person with ordinary skill in the art.

Manufacturing methods of polyurethane foam described in JP 2005-534770 T, JP 2005-534770 T, and JP 2010-535931 T;

Manufacturing process of open cell polyurethane described in JP 2010-539280 T;

Sealing material containing urethane foam described in JP 2012-246397 A, JP 2009-265425 A, and the like;

Manufacturing of urethane foam described in JP 2012-082273 A, JP 2010-247532 A, JP 2010-195870 A, JP 2002-137234 A, and the like Polyurethane foam obtained by applying the polyether-polysiloxane block copolymer composition of the present invention in manufacturing methods of the aforementioned patent publications and the like is included within the scope of the present invention. Furthermore, it goes without saying that the scope of the invention of a polyurethane foam using the polyether-polysiloxane block copolymer composition of the present invention is not restricted thereto.

Cosmetic Raw Material and Cosmetic

The polyether-polysiloxane block copolymer composition of the present invention is useful as a cosmetic raw material, and has advantages where production is possible at a relatively low cost in an industrial production process and can be supplied at a high added value and low cost, as described above.

Furthermore, the present invention relates to a cosmetic containing the polyether-polysiloxane block copolymer composition. Examples of cosmetics can include known cosmetics in the related art containing polyether-modified silicone, glycerin-modified silicone, or polyether-polysiloxane block copolymer, and combinations and applications of a described cosmetic raw material component and similar component.

More specific example includes skin cosmetics or hair cosmetics containing the polyether-polysiloxane block copolymer composition according to the present invention.

The form of a skin cosmetic according to the present invention is not particularly limited so long as the polyether-polysiloxane block copolymer composition according to the present invention is included, and may be a solution, cream, solid, semi-solid, gel, water-in-oil, or oil-in-water type solutions. Specific examples of the skin cosmetic according to the present invention include toilet water, emulsions, creams, sunscreen emulsions, sunscreen creams, hand creams, cleansing compositions, massage lotions, cleansing agents, antiperspirants, deodorants, and other basic cosmetic products; foundations, make-up bases, blushers, rouges, eye shadows, eye liners, mascaras, nail enamels, and other make-up cosmetic products; and the like.

Similarly, a hair cosmetic according to the present invention can be used in various forms so long as the polyether-polysiloxane block copolymer composition according to the present invention is included. For example, the hair cosmetics may be used after dissolving or dispersing in an alcohol, a hydrocarbon, a volatile cyclic silicone, or the like, or can be used in the form of an emulsion by dispersing in water using an emulsifier. Furthermore, the cosmetic can be used as a spray by using propane, butane, trichloromonofluoromethane, dichlorodifluoromethane, dichlorotetrafluoroethane, carbonic acid gas, nitrogen gas, or other propellant. Various forms thereof can include shampooing agents, rinsing agents, setting lotions, hair sprays, permanent wave agents, mousses, hair colorants, and the like.

The cosmetics of the present invention can optionally add components used in normal cosmetics, water, powders or coloring agents, alcohols, water-soluble polymers, film-forming agents, oil agents, oil-soluble gelling agents, organo-modified clay minerals, surfactants, resins, UV absorbers, moisturizing agents, preservatives, antibacterial agents, fragrances, salts, antioxidants, pH adjusters, chelating agents, refreshing agents, anti-inflammatory agents, skin beautifying components (whitening agents, cell activating agents, skin roughness improving agents, blood circulation promoters, skin astringents, antiseborrheic agents, and the like), vitamins, amino acids, nucleic acids, hormones, clathrate compounds, and the like; bioactive substances, and fragrances, and can be used in place of the polyether-polysiloxane block copolymer according to the present invention in various known cosmetic formulations in the related art where a polyether-modified silicone, glycerin-modified silicone, sugar-modified silicone, polyether-polysiloxane block copolymer, or the like is added. These cosmetics are not particularly limited. Note that a description in Patent Literature 11 (WO 2011/049248) can be referenced for details of various components that can be added to the cosmetic of the present invention or formulation examples that can be used.

Formulations Already Disclosed in Previous Applications

The polyether-polysiloxane block copolymer composition according to the present invention can be used in various external preparations and cosmetics. Specific formulation example include formulations where an appropriate component corresponding to a silicone-based surfactant in a formulation example of various cosmetics and external preparations disclosed in the examples and the like described by the applicants in Patent Literature 11 (WO 2011/049248) is replaced by the aforementioned polyether-polysiloxane block copolymer composition according to the present invention, which are included in the scope of the present invention as formulation examples of the cosmetic and external preparation according to the present invention. It goes without saying that the formulation examples of the cosmetic and external preparation according to the present invention is not limited thereto, and formulations where a silicone-based surfactant of a cosmetic containing a known silicone-based surfactant (polyether-modified silicone, glycerin-modified silicone, or polyether-polysiloxane block copolymer) in the related art is substituted by the polyether-polysiloxane block copolymer composition according to the present invention are included in the scope of the present invention as formulations examples of the cosmetic and external preparation according to the present invention.

EXAMPLES

Hereinafter, the present invention will be further described in detail based on examples and comparative examples, but the present invention is not limited thereto. Note that in the following composition formulas, a $Me_3SiO$ group (or $Me_3Si$ group) is expressed as "M", a $Me_2SiO$ group is expressed as "D", a MeHSiO group is expressed as "$M^H$", and units where a methyl group in M and D is modified by any substitution group is expressed as $M^R$ and $D^R$. Furthermore, IPA is isopropanol.

Example 1-1

75.25 g of methyl hydrogen polysiloxane as expressed by average composition formula $M^H D_{20} M^H$, 174.75 g of a bis-methallyl polyether as expressed by average composition formula $CH_2=C(CH_3)CH_2-O(C_2H_4O)_{33}(C_3H_6O)_{25}-CH_2-C(CH_3)=CH_2$, 250 g of dipropylene glycol monobutyl ether (BDPG), and 0.25 g of natural vitamin E were inserted into a 1 L reactor and then heated to 80 to 90° C. while stirring under a nitrogen flow. 0.56 g of an IPA solution (Pt concentration: 0.45 wt %) of a platinum-2,4,6,8-tetraemethyl-2,4,6,8-tetravinyl tetrasiloxane complex was added and a reaction was performed for 2.5 hours. 1 g of the reaction liquid was collected, and the reaction was confirmed to be completed using an alkali decomposition gas generation method. A straight chain organopolysiloxane-polyether block copolymer at least containing a structural unit as expressed by the average composition formula:

[Chemical Formula 6]

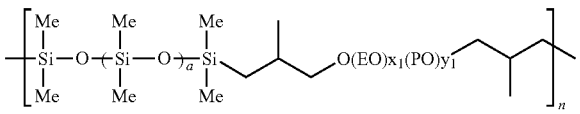

(where a=20, x1=33, y1=25, and n=6)
and BDPG were included at a 50:50 ratio to obtain a liquid polyether-polysiloxane block copolymer composition. Note that the average composition formula is simply expressed, but the molar ratio of C=C groups and Si—H groups of raw material is approximately 7:6, and therefore, both terminals of the copolymer have a form blocked by a polyether (=terminal functional group is a methallyl group bonded to a polyether). Furthermore, a portion of the Si—H groups in the reaction can cause a dehydrogenative condensation reaction with a hydroxyl group of the IPA or BDPG, and therefore, a portion of the copolymer terminal is considered to include a structure of SiO-iPr or SiO—$R^1$ ($R^1$ represents a BDPG residual group). Note that herein, a polyether portion is a random adduct of ethylene oxide and propylene oxide.

Example 1-2

An experiment was performed similarly to Example 1-1 except that the BDPG was substituted with a propylene glycol monobutyl ether (BPG). Behaviors such as reactivity and the like in the synthesis reaction of the straight chain organopolysiloxane-polyether block copolymer was similar to Example 1-1.

Example 2-1

85.55 g of methyl hydrogen polysiloxane as expressed by average composition formula $M^H D_{20} M^H$, 164.45 g of a bis-methallyl polyether as expressed by average composition formula $CH_2$=$C(CH_3)CH_2$—$O(C_2H_4O)_{33}(C_3H_6O)_{25}$—$CH_2$—$C(CH_3)$=$CH_2$, 250 g of dipropylene glycol monobutyl ether (BDPG), and 0.25 g of natural vitamin E were inserted into a 1 L reactor and then heated to 80 to 90° C. while stirring under a nitrogen flow. 0.056 g of an IPA solution (Pt concentration: 4.5 wt %) of a platinum-2,4,6,8-tetraemethyl-2,4,6,8-tetravinyl tetrasiloxane complex was added and a reaction was performed for 3 hours. 1 g of the reaction liquid was collected, and the reaction was confirmed to be completed using an alkali decomposition gas generation method. A straight chain organopolysiloxane-polyether block copolymer at least containing a structural unit as expressed by the average composition formula:

[Chemical Formula 7]

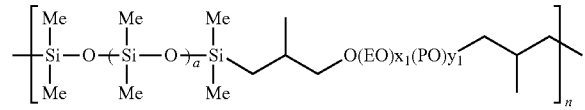

(where a=20, x1=33, y1=25, and n>10)
and BDPG were included at a 50:50 ratio to obtain a liquid polyether-polysiloxane block copolymer composition. Note that the average composition formula is simply expressed, but the molar ratio of C=C groups and Si—H groups of raw material is approximately 1:1 and polyether is slightly in excess, and therefore, both terminals of the copolymer have a form blocked by a polyether (=terminal functional group is a methallyl group bonded to a polyether). Furthermore, a portion of the Si—H groups in the reaction can cause a dehydrogenative condensation reaction with a hydroxyl group of the IPA or BDPG, and therefore, a portion of the copolymer terminal is considered to include a structure of SiO-iPr or SiO—$R^1$ ($R^1$ represents a BDPG residual group). Note that herein, a polyether portion is a random adduct of ethylene oxide and propylene oxide.

Example 2-2

An experiment was performed similarly to Example 2-1 except that the BDPG was substituted with a propylene glycol monobutyl ether (BPG). Behaviors such as reactivity and the like in the synthesis reaction of the straight chain organopolysiloxane-polyether block copolymer was similar to Example 2-1.

Example 2-3 Without Solvent 84.25 g of methyl hydrogen polysiloxane as expressed by average composition formula $M^H D_{20} M^H$, 165.75 g of a bis-methallyl polyether as expressed by average composition formula $CH_2$=$C(CH_3)CH_2$—$O(C_2H_4O)_{33}(C_3H_6O)_{25}$—$CH_2$—$C(CH_3)$=$CH_2$, and 0.25 g of natural vitamin E were inserted into a 1 L reactor and then heated to 85 to 95□ while stirring under a nitrogen flow. When 0.56 g of an IPA solution (Pt concentration: 0.45 wt %) of a platinum-2,4,6,8-tetraemethyl-2,4,6,8-tetravinyl tetrasiloxane complex was added and a reaction was performed for 2.5 hour, the solution changed into a very high viscosity liquid. Next, when 1 g of reaction liquid was collected and diluted with toluene to reduce the viscosity, and then the reaction rate was confirmed by an alkali decomposition gas generation method, the gas generation amount was a trace amount, and therefore, the reaction was determined to be essentially completed. Next, 250 g of dipropylene glycol monobutyl ether (BDPG) was added to the reaction liquid, mixed homogenization was performed for 1 hour, and then when sampling was performed as a precaution to examine the reaction rate, approximately 36 ppm of silicon-bonded hydrogen atoms were detected. Therefore, after aging was performed for 3.5 hours at 85 to 95° C., the reaction was completed. A straight chain organopolysiloxane-polyether block copolymer at least containing a structural unit as expressed by the average composition formula:

[Chemical Formula 8]

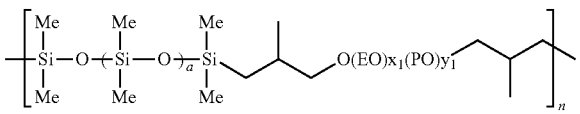

(where a=20, x1=33, y1=25, and n>10)
and BDPG were included at a 50:50 ratio to obtain a liquid polyether-polysiloxane block copolymer composition. Note that the average composition formula is simply expressed, but the molar ratio of C=C groups and Si—H groups of raw material is approximately 1:1 and polyether is slightly in excess, and therefore, both terminals of the copolymer have a form blocked by a polyether (=terminal functional group is a methallyl group bonded to a polyether). Furthermore, a portion of the Si—H groups in the reaction can cause a dehydrogenative condensation reaction with a hydroxyl group of the IPA or BDPG, and therefore, a portion of the copolymer terminal is considered to include a structure of SiO-iPr or SiO—$R^1$ ($R^1$ represents a BDPG residual group). Note that herein, a polyether portion is a random adduct of ethylene oxide and propylene oxide.

Example 2-4 Solvent Substitution Method 84.25 g of methyl hydrogen polysiloxane as expressed by average composition formula $M^H D_{20} M^H$, 165.75 g of a bis-methallyl polyether as expressed by average composition formula $CH_2$=$C(CH_3)CH_2$—$O(C_2H_4O)_{33}(C_3H_6O)_{25}$—$CH_2$—$C(CH_3)$=$CH_2$, 250 g of toluene, and 0.25 g of natural vitamin E were inserted into a 1 L reactor and then heated to 80 to 90□ while stirring under a nitrogen flow. 0.56 g of an IPA solution (Pt concentration: 0.45 wt %) of a platinum-2,4,6,8-tetraemethyl-2,4,6,8-tetravinyl tetrasiloxane complex was added and a reaction was performed for 2 hours. 1 g of the reaction liquid was collected, and the reaction was confirmed to be completed using an alkali decomposition gas generation method. The reaction system was further heated to 125° C. while gradually reducing pressure, and then the toluene was gradually distilled while paying attention to bumping caused by foaming. Pressure was restored at a stage where approximately ¾ of the toluene was removed, and after 250 g of dipropylene glycol monobutyl ether (BDPG) was added to the reaction system, the pressure was again reduced and the remaining toluene was carefully distilled. The weight ratio of the copolymer and BDPG was 50:50 at a point in time where distillation of the toluene was completed, but the contents at this stage had a very high viscosity, and thus stirring was difficult. Therefore, 250 g×2 times of BDPG was further added and introduced to perform dilution. A straight chain organopolysiloxane-polyether block copolymer at least containing a structural unit as expressed by the average composition formula:

[Chemical Formula 9]

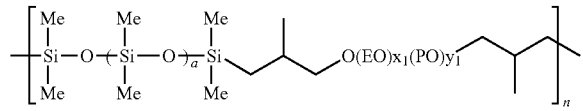

(where a=20, x1=33, y1=25, and n>10)
and BDPG were included at a 33:67 ratio to obtain a liquid polyether-polysiloxane block copolymer composition. After confirming the contents of the flask the next morning, the viscosity was found to still be very high at room temperature, and handling was difficult. Therefore, 60 g of the contents of the flask were dispensed into a 200 mL glass bottle, 20 g of BDPG was added thereto, and then mixing was performed at 1600 rpm×5 minutes using a homodisper mixer. Thereby, a straight chain organopolysiloxane-polyether block copolymer at least containing a structural unit as expressed by the aforementioned average composition formula and BDPG were included at a 25:75 ratio to obtain a liquid polyether-polysiloxane block copolymer composition. Note that the average composition formula is simply expressed, but the molar ratio of C=C groups and Si—H groups of raw material is approximately 1:1 and polyether is slightly in excess, and therefore, both terminals of the copolymer have a form blocked by a polyether (=terminal functional group is a methallyl group bonded to a polyether). Furthermore, a portion of the Si—H groups in the reaction can cause a dehydrogenative condensation reaction with a hydroxyl group of the IPA, and therefore, a portion of the copolymer terminal is considered to include a structure of SiO-iPr. Note that herein, a polyether portion is a random adduct of ethylene oxide and propylene oxide.

Example 2-5

However, BDPG was changed to 2-hexyl-1-decanol (HDL) and then an experiment was performed in accordance with the aforementioned Example 2-1. Behaviors such as reactivity and the like in the synthesis reaction of the straight chain organopolysiloxane-polyether block copolymer was similar to Example 2-1.

Example 3-1

102.15 g of methyl hydrogen polysiloxane as expressed by average composition formula $M^HD_{20}M^H$, 231.2 g of a bis-methallyl polyether as expressed by average composition formula $CH_2=C(CH_3)CH_2-O(C_2H_4O)_{33}(C_3H_6O)_{25}-CH_2-C(CH_3)=CH_2$, 166.7 g of BDPG, and 0.25 g of natural vitamin E were inserted into a 1 L reactor and then heated to 100 to 110□ while stirring under a nitrogen flow. 0.74 g of an IPA solution (Pt concentration: 0.45 wt %) of a platinum-2,4,6,8-tetramethyl-2,4,6,8-tetravinyl tetrasiloxane complex was added and a reaction was performed for 3 hours. 1 g of the reaction liquid was collected, and the reaction was confirmed to be completed using an alkali decomposition gas generation method. A straight chain organopolysiloxane-polyether block copolymer at least containing a structural unit as expressed by the average composition formula:

[Chemical Formula 10]

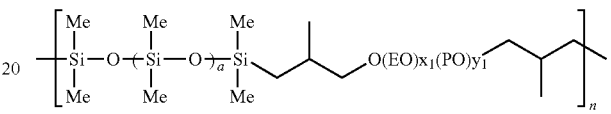

(where a=20, x1=33, y1=25, and n=6)
and BDPG were included at a 67:33 ratio to obtain a liquid polyether-polysiloxane block copolymer composition. Note that the average composition formula is simply expressed, but the molar ratio of C=C groups and Si—H groups of raw material is approximately 7:6, and therefore, both terminals of the copolymer have a form blocked by a polyether (=terminal functional group is a methallyl group bonded to a polyether). Furthermore, a portion of the Si—H groups in the reaction can cause a dehydrogenative condensation reaction with a hydroxyl group of the IPA or BDPG, and therefore, a portion of the copolymer terminal is considered to include a structure of SiO-iPr or SiO—$R^1$ ($R^1$ represents a BDPG residual group). Note that herein, a polyether portion is a random adduct of ethylene oxide and propylene oxide.

Example 3-2

112.9 g of methyl hydrogen polysiloxane as expressed by average composition formula $M^HD_{20}M^H$, 262.1 g of a bis-methallyl polyether as expressed by average composition formula $CH_2=C(CH_3)CH_2-O(C_2H_4O)_{33}(C_3H_6O)_{25}-CH_2-C(CH_3)=CH_2$, 125 g of propylene glycol monobutyl ether (BPG), and 0.25 g of natural vitamin E were inserted into a 1 L reactor and then heated to 90° C. while stirring under a nitrogen flow. 0.83 g of an IPA solution (Pt concentration: 0.45 wt %) of a platinum-2,4,6,8-tetraemethyl-2,4,6,8-tetravinyl tetrasiloxane complex was added and a reaction was performed for 3 hours at 100° C. 1 g of the reaction liquid was collected, and the reaction was confirmed to be completed using an alkali decomposition gas generation method. A straight chain organopolysiloxane-polyether block copolymer at least containing a structural unit as expressed by the average composition formula:

[Chemical Formula 11]

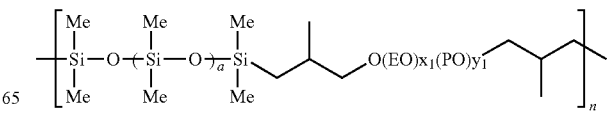

(where a=20, x1=33, y1=25, and n=6) and BPG were included at a 75:25 ratio to obtain a liquid polyether-polysiloxane block copolymer composition. Note that the average composition formula is simply expressed, but the molar ratio of C=C groups and Si—H groups of raw material is approximately 7:6, and therefore, both terminals of the copolymer have a form blocked by a polyether (=terminal functional group is a methallyl group bonded to a polyether). Furthermore, a portion of the Si—H groups in the reaction can cause a dehydrogenative condensation reaction with a hydroxyl group of the IPA or BPG, and therefore, a portion of the copolymer terminal is considered to include a structure of SiO-iPr or SiO—$R^1$ ($R^1$ represents a BPG residual group). Note that herein, a polyether portion is a random adduct of ethylene oxide and propylene oxide.

Example 4-1

76.75 g of methyl hydrogen polysiloxane as expressed by average composition formula $M^H D_{20} M^H$, 173.25 g of a bis-methallyl polyether as expressed by average composition formula $CH_2=C(CH_3)CH_2-O(C_2H_4O)_{52}(C_3H_6O)_{10}-CH_2-C(CH_3)=CH_2$, 250 g of BDPG, and 0.25 g of natural vitamin E were inserted into a 1 L reactor and then heated to 85 to 95□ while stirring under a nitrogen flow. 0.56 g of an IPA solution (Pt concentration: 0.45 wt %) of a platinum-2,4,6,8-tetraemethyl-2,4,6,8-tetravinyl tetrasiloxane complex was added and a reaction was performed for 2 hours. 1 g of the reaction liquid was collected, and the reaction was confirmed to be completed using an alkali decomposition gas generation method. A straight chain organopolysiloxane-polyether block copolymer at least containing a structural unit as expressed by the average composition formula:

[Chemical Formula 12]

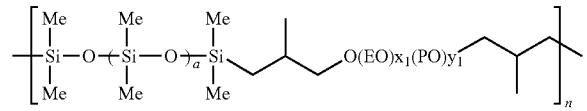

(where a=20, x1=52, y1=10, and n=6) and BDPG were included at a 50:50 ratio to obtain a liquid polyether-polysiloxane block copolymer composition. Note that the average composition formula is simply expressed, but the molar ratio of C=C groups and Si—H groups of raw material is approximately 7:6, and therefore, both terminals of the copolymer have a form blocked by a polyether (=terminal functional group is a methallyl group bonded to a polyether). Furthermore, a portion of the Si—H groups in the reaction can cause a dehydrogenative condensation reaction with a hydroxyl group of the IPA or BDPG, and therefore, a portion of the copolymer terminal is considered to include a structure of SiO-iPr or SiO—$R^1$ ($R^1$ represents a BDPG residual group). Note that herein, a polyether portion is a random adduct of ethylene oxide and propylene oxide.

Example 4-2

An experiment was performed similarly to Example 4-1 except that the BDPG was substituted with a propylene glycol monobutyl ether (BPG). Behaviors such as reactivity and the like in the synthesis reaction of the straight chain organopolysiloxane-polyether block copolymer was similar to Example 4-1.

Example 5-1

60 g of the polyether-polysiloxane block copolymer composition obtained in the aforementioned Example 3-1 and 20 g of polypropylene glycol monobutyl ether {BPPG-13} as expressed by n-BuO$(C_3H_6O)_{13}$—H were inserted in a 200 mL glass bottle, and then mixing was performed at 1600 rpm×5 minutes using a homodisper mixer at room temperature. Thereby, a liquid polyether-polysiloxane block copolymer composition having an abundance ratio of copolymer: BDPG:{BPPG-13}=2:1:1.

Example 5-2

60 g of the gum-like polyether-polysiloxane block copolymer composition obtained in the aforementioned Comparative Example 3-1 and 20 g of polypropylene glycol monobutyl ether {BPPG-13} as expressed by n-BuO$(C_3H_6O)_{13}$—H were inserted in a 200 mL glass bottle, and the bottle was stopped, and heating and shaking operations were repeated to partially dissolve the gum. Thereafter, mixing was performed to homogenize at 1600 rpm×5 minutes at room temperature using a homodisper mixer. Thereby, a liquid polyether-polysiloxane block copolymer composition having an abundance ratio of copolymer: BDPG:{BPPG-13}=2:1:5.

Example 5-3

40 g of the polyether-polysiloxane block copolymer composition obtained in the aforementioned Example 2-4 and 40 g of polypropylene glycol (PPG-7) as expressed by HO$(C_3H_6O)_7$—H were inserted in a 200 mL glass bottle, and then mixing was performed at 1600 rpm×5 minutes using a homodispersion mixer at room temperature. Thereby, a liquid polyether-polysiloxane block copolymer composition having an abundance ratio of copolymer: BDPG:{PPG-7}=1:3:4.

Example 5-4

40 g of the polyether-polysiloxane block copolymer composition obtained in the aforementioned Example 3-2 and 35 g of dodecylbenzene (DB) were inserted in a 200 mL glass bottle, and then mixing was performed at 1600×5 minutes using a homodisper at room temperature. Thereby, a liquid polyether-polysiloxane block copolymer composition having an abundance ratio of copolymer:BPG:DB=3:1:3.5.

Comparative Example 1-1

75.25 g of methyl hydrogen polysiloxane as expressed by average composition formula $M^H D_{20} M^H$, 174.75 g of a bis-methallyl polyether as expressed by average composition formula $CH_2=C(CH_3)CH_2-O(C_2H_4O)_{33}(C_3H_6O)_{25}-CH_2-C(CH_3)=CH_2$, 250 g hexylene glycol (HG, separate name: 2-methylpentane-2,4-diol), and 0.25 g of natural vitamin E were inserted into a 1 L reactor and then heated to 80 to 90□ while stirring under a nitrogen flow. 0.56 g of an IPA solution (Pt concentration: 0.45 wt %) of a platinum-2,4,6,8-tetraemethyl-2,4,6,8-tetravinyl tetrasiloxane complex was added and a reaction was performed for 1.5 to 2 hours. Next, 1 g of the reaction liquid was collected, and when the reaction rate was confirmed by an alkali decomposition gas generation method (the remaining Si—H groups are decomposed using a KOH ethanol/water solution, and the reaction rate is calculated from the volume of the produced hydrogen gas), the reaction was found to be slow and not completed. Therefore, as a result of heating the reaction liquid to 115 to 120° C. and then continuing the reaction for 2 to 3 hours, the reaction was completed. A straight chain organopolysiloxane-polyether block copolymer at least containing a structural unit as expressed by the average composition formula:

[Chemical Formula 13]

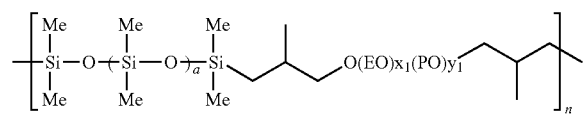

(where a=20, x1=33, y1=25, and n=6)
and HG were included at a 50:50 ratio to obtain a liquid polyether-polysiloxane block copolymer composition. Note that the average composition formula is simply expressed, but the molar ratio of C=C groups and Si—H groups of raw material is approximately 7:6, and therefore, both terminals of the copolymer have a form blocked by a polyether. Furthermore, a portion of the Si—H groups in the reaction can cause a dehydrogenative condensation reaction with a hydroxyl group of the IPA or HG, and therefore, a portion of the copolymer terminal is considered to include a structure of SiO-iPr or SiO—$R^1$ ($R^1$ represents a HG residual group). Note that herein, a polyether portion is a random adduct of ethylene oxide and propylene oxide.

Comparative Example 1-2 to Comparative Example 1-6

An experiment was performed similarly to Comparative Example 1-1 except that the HG was changed to another diol compound with a low molecular weight below.

Comparative Example 1-2: Propylene glycol (PG)

Comparative Example 1-3: Dipropylene glycol (DPG)

Comparative Example 1-4: Tripropylene glycol (TPG)

Comparative Example 1-5: 1,2-Butylene glycol (1,2-BG)

Comparative Example 1-6: 1,3-Butylene glycol (1,3-BG)

In the aforementioned experiments, behaviors such as reactivity and the like in the synthesis reaction of the straight chain organopolysiloxane-polyether block copolymer was similar to Comparative Example 1-1.

Comparative Example 1-7

75.25 g of methyl hydrogen polysiloxane as expressed by average composition formula $M^H D_{20} M^H$, 174.75 g of a bis-methallyl polyether as expressed by average composition formula $CH_2=C(CH_3)CH_2-O(C_2H_4O)_{33}(C_3H_6O)_{25}-CH_2-C(CH_3)=CH_2$, 250 g of polypropylene glycol (PPG-7) as expressed by $HO(C_3H_6O)_7-H$, and 0.25 g of natural vitamin E were inserted into a 1 L reactor and then heated to 80 to 90° C. while stirring under a nitrogen flow. 0.56 g of an IPA solution (Pt concentration: 0.45 wt %) of a platinum-2,4,6,8-tetraemethyl-2,4,6,8-tetravinyl tetrasiloxane complex was added and a reaction was performed for 1.5 to 2 hours. 1 g of the reaction liquid was collected, and when the reaction rate was confirmed using an alkali decomposition gas generation method, the reaction was found to not have advanced at all. Therefore, two times the amount of a catalyst was further added, the reaction liquid was heated to 115 to 120° C., the reaction was continued for 2 to 3 hours, and the reaction rate was similarly confirmed, but the reaction did not advance at all. When heating and stirring were stopped, the reaction liquid was left to stand overnight, and then the contents of the flask were confirmed, the contents were found to be separated into two layers of a siloxane layer and polyether ether layer, and synthesis of the copolymer was found to be impossible under this condition.

Comparative Example 1-8

An experiment was performed in accordance with the aforementioned Comparative Example 1-7 except that PPG-7 was changed to polypropylene glycol monobutyl ether as expressed by $n-BuO(C_3H_6O)_{13}-H$. However, the hydrosilylation react similarly did not advance at all, two-layer separation of a siloxane layer and polyether layer was confirmed, and synthesis of the copolymer was found to be impossible.

Comparative Example 1-9

75.25 g of methyl hydrogen polysiloxane as expressed by average composition formula $M^H D_{20} M^H$, 174.75 g of a bis-methallyl polyether as expressed by average composition formula $CH_2=C(CH_3)CH_2-O(C_2H_4O)_{33}(C_3H_6O)_{25}-CH_2-C(CH_3)=CH_2$, 250 g of diethylene glycol monobutyl ether (BDEG), and 0.25 g of natural vitamin E were inserted into a 1 L reactor and then heated to 80 to 90° C. while stirring under a nitrogen flow. 0.56 g of an IPA solution (Pt concentration: 0.45 wt %) of a platinum-2,4,6,8-tetraemethyl-2,4,6,8-tetravinyl tetrasiloxane complex was added and a reaction was performed for 3 hours. 1 g of the reaction liquid was collected, and the reaction was confirmed to be completed using an alkali decomposition gas generation method. Thereby, similar to Comparative Example 1, a straight chain organopolysiloxane-polyether block copolymer and BDEG were included at a 50:50 ratio to obtain a liquid polyether-polysiloxane block copolymer composition.

Comparative Example 2-1

75.25 g of methyl hydrogen polysiloxane as expressed by average composition formula $M^H D_{20} M^H$, 174.75 g of a bis-methallyl polyether as expressed by average composition formula $CH_2=C(CH_3)CH_2-O(C_2H_4O)_{33}(C_3H_6O)_{25}-CH_2-C(CH_3)=CH_2$, 375 g of toluene, and 0.25 g of natural vitamin E were inserted into a 1 L reactor and then heated to 70 to 80□ while stirring under a nitrogen flow. 0.05 g of a 10% IPA solution of chloroplatinic acid (Pt concentration: 3.8 wt %) was added, and a reaction was performed for 2 hours. 1 g of the reaction liquid was collected, and the reaction was confirmed to be completed using an alkali decomposition gas generation method. The reaction system was further heated to 125° C. while gradually reducing pressure, and then the toluene was gradually distilled while paying attention to bumping caused by foaming. Pressure was restored at a stage where approximately ¾ of the toluene was removed, and after 125 g of polypropylene glycol monobutyl ether 1 BPPG-131 as expressed by n-BuO($C_3H_6O$)$_{13}$—H was added to the reaction system, the pressure was again reduced and the remaining toluene was carefully distilled. Pressure was restored, 125 g of BPPG-13 was added and then homogeneously mixed. A straight chain organopolysiloxane-polyether block copolymer at least containing a structural unit as expressed by the average composition formula:

[Chemical Formula 14]

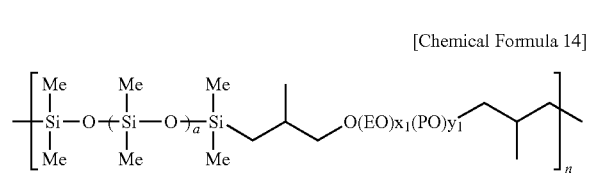

(where a=20, x1=33, y1=25, and n=6)
and BPPG-13 were included at a 50:50 ratio to obtain a liquid polyether-polysiloxane block copolymer composition. Note that the average composition formula is simply expressed, but the molar ratio of C=C groups and Si—H groups of raw material is approximately 7:6, and therefore, both terminals of the copolymer have a form blocked by a polyether. Furthermore, a portion of the Si—H groups in the reaction can cause a dehydrogenative condensation reaction with a hydroxyl group of the IPA, and therefore, a portion of the copolymer terminal is considered to include a structure of SiO-iPr. Note that herein, a polyether portion is a random adduct of ethylene oxide and propylene oxide.

Comparative Example 2-2

84.25 g of methyl hydrogen polysiloxane as expressed by average composition formula $M^H D_{20} M^H$, 165.75 g of a bis-methallyl polyether as expressed by average composition formula $CH_2=C(CH_3)CH_2-O(C_2H_4O)_{33}(C_3H_6O)_{25}-CH_2-C(CH_3)=CH_2$, 250 g of benzyl alcohol (BZL), and 0.25 g of natural vitamin E were inserted into a 1 L reactor and then heated to 80 to 90☐ while stirring under a nitrogen flow. 0.56 g of an IPA solution (Pt concentration: 0.45 wt %) of a platinum-2,4,6,8-tetraemethyl-2,4,6,8-tetravinyl tetrasiloxane complex was added and a reaction was performed for 1.5 hours, but the appearance was strongly cloudy, and the reaction was observed to not have advanced. Therefore, the reaction temperature was set to 100° C. and aging was further performed for 2 hours, but the reaction rate and appearance did not change. Even though the same amount of a catalyst was added, the reaction temperature was increased to 120 to 125° C., and aging was further performed for 7 hours, the reaction was not completed, and therefore, the experiment was stopped.

Comparative Example 3-1

76.75 g of methyl hydrogen polysiloxane as expressed by average composition formula $M^H D_{20} M^H$, 173.25 g of a bis-methallyl polyether as expressed by average composition formula $CH_2=C(CH_3)CH_2-O(C_2H_4O)_{52}(C_3H_6O)_{10}-CH_2-C(CH_3)=CH_2$, 250 g hexylene glycol (HG, separate name: 2-methylpentane-2,4-diol), and 0.25 g of natural vitamin E were inserted into a 1 L reactor and then heated to 85 to 110☐ while stirring under a nitrogen flow. 0.56 g of an IPA solution (Pt concentration: 0.45 wt %) of a platinum-2,4,6,8-tetraemethyl-2,4,6,8-tetravinyl tetrasiloxane complex was added and a reaction was performed for 2 hours. 1 g of the reaction liquid was collected, and when the reaction rate was confirmed using an alkali decomposition gas generation method, the reaction was found to be slow and not completed. Therefore, as a result of heating the reaction liquid to 120° C. and then continuing the reaction for 7 hours, the reaction was completed. A straight chain organopolysiloxane-polyether block copolymer at least containing a structural unit as expressed by the average composition formula:

[Chemical Formula 15]

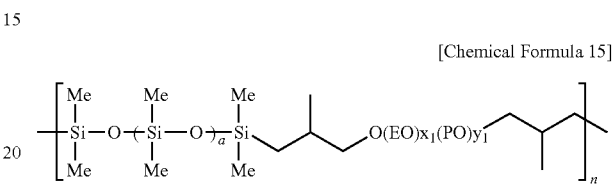

(where a=20, x1=52, y1=10, and n=6)
and HG were included at a 50:50 ratio to obtain a liquid polyether-polysiloxane block copolymer composition. Note that the average composition formula is simply expressed, but the molar ratio of C=C groups and Si—H groups of raw material is approximately 7:6, and therefore, both terminals of the copolymer have a form blocked by a polyether. Furthermore, a portion of the Si—H groups in the reaction can cause a dehydrogenative condensation reaction with a hydroxyl group of the IPA or HG, and therefore, a portion of the copolymer terminal is considered to include a structure of SiO-iPr or SiO—$R^1$ ($R^1$ represents a HG residual group). Note that herein, a polyether portion is a random adduct of ethylene oxide and propylene oxide.

Comparative Example 3-2

An experiment was performed similarly to Comparative Example 3-1 except that the HG was substituted with a diethylene glycol monobutyl ether (BDEG). However, the reactivity during the synthesis experiment was inferior, which was similar to Comparative Example 3-1.

Physical Properties of Composition According to Examples and Comparative Examples The following Table 1 and Table 2 show the design structures, contents, appearances, kinematic viscosity (mm2/s) at 25° C., and the like of the obtained compositions for the aforementioned Examples 1-1 and 1-2, Examples 2-1 to 2-5, Examples 3-1 and 3-2, Examples 4-1 and 4-2, Examples 5-1 to 5-3, Comparative Examples 1-1 to 1-9, Comparative Examples 2-1 and 2-2, and Comparative Examples 3-1 and 3-2.

Note that all compositions other than Comparative Example 1-7 and 1-8 which did not synthesize at all contain a straight chain organopolysiloxane-polyether block copolymer as expressed below as component (A).

[Chemical Formula 16]

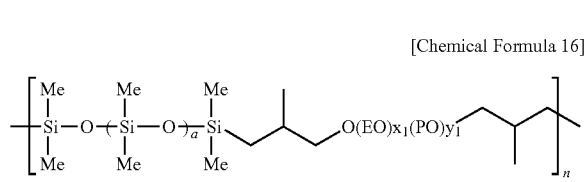

using the HG as a reaction solvent has strong turbidity and slow advancement of hydrosilylation, and therefore, HG is difficult to use in an industrial production process.

Furthermore, polyglycols in the related art used as a diluting agent of the (AB)n type polyether-polysiloxane block copolymer could not be used as a synthesizing agent of the copolymer. This is because a hydrosilylation reaction did not advance at all. This is because the polyglycols have a high molecular weight, and therefore, the ability to compatibilize the organopolysiloxane containing a SiH group on both terminals and polyether containing a methallyl group on both terminals, and the effect of increasing chances of contacting or mixing both by reducing the viscosity of the system are inferior. Furthermore, alkali catalysts are often used in a manufacturing process of the polyglycols, and therefore, there is considered to be a high possibility that a

TABLE 1

Design structures, contents, and the like of samples obtained in the examples

| Example No. | Composition Properties | | | Structure of Copolymer (A) | | | | (B) | (C) | A/B/C |
|---|---|---|---|---|---|---|---|---|---|---|
| | Reactivity | Appearance | Viscosity | a | x1 | y1 | n | | | |
| 1-1 | Favorable | Transparent | 1700 | 20 | 33 | 25 | 6 | BDPG | None | 50/50/0 |
| 1-2 | Favorable | Transparent | 500 | 20 | 33 | 25 | 6 | BPG | None | 50/50/0 |
| 2-1 | Favorable | Transparent | 6600 | 20 | 33 | 25 | >10 | BDPG | None | 50/50/0 |
| 2-2 | Favorable | Transparent | 1200 | 20 | 33 | 25 | >10 | BPG | None | 50/50/0 |
| 2-3 | Pass | Semi-transparent | 50400 | 20 | 33 | 25 | >10 | BPDG | None | 50/50/0 |
| 2-4 | Favorable | Transparent | 17500 | 20 | 33 | 25 | >10 | BPDG | None | 25/75/0 |
| 2-5 | Favorable | Semi-transparent | 12300 | 20 | 33 | 25 | >10 | HDL | None | 50/50/0 |
| 3-1 | Pass | Semi-transparent | 15000 | 20 | 33 | 25 | 6 | BDPG | None | 67/33/0 |
| 3-2 | Pass | Semi-transparent | 21600 | 20 | 33 | 25 | 6 | BPG | None | 75/25/0 |
| 4-1 | Favorable | Semi-transparent | 4500 | 20 | 52 | 10 | 6 | BDPG | None | 50/50/0 |
| 4-2 | Favorable | Transparent | 1500 | 20 | 52 | 10 | 6 | BPG | None | 50/50/0 |
| 5-1 | Pass | Semi-transparent | 2300 | 20 | 33 | 25 | 6 | BDPG | BPPG-13 | 50/25/25 |
| 5-2 | Pass | Transparent | 9100 | 20 | 33 | 25 | >10 | BDPG | BPPG-13 | 25/12/63 |
| 5-3 | Favorable | Transparent | 2500 | 20 | 33 | 25 | >10 | BDPG | PPG-7 | 12/38/50 |
| 5-4 | Pass | Semi-transparent | 1000 | 20 | 33 | 25 | 6 | BPG | DB* Optional Components | 40/13/47 |

Note
*Dodecylbenzene

TABLE 2

Design structures, contents, and the like of samples obtained in the comparative examples

| Comparative Example No. | Composition Properties | | | Structure of Copolymer (A) | | | | (B') | (C) | A/B/C |
|---|---|---|---|---|---|---|---|---|---|---|
| | Reactivity | Appearance | Viscosity | a | x1 | y1 | n | | | |
| 1-1 | Defective | Opaque | — | 20 | 33 | 25 | 6 | HG | None | 50/50/0 |
| 1-2 | Defective | Separated | — | 20 | 33 | 25 | 6 | PG | None | 50/50/0 |
| 1-3 | Defective | Separated | — | 20 | 33 | 25 | 6 | DPG | None | 50/50/0 |
| 1-4 | Defective | Separated | — | 20 | 33 | 25 | 6 | TPG | None | 50/50/0 |
| 1-5 | Defective | Separated | — | 20 | 33 | 25 | 6 | 1,2BG | None | 50/50/0 |
| 1-6 | Defective | Turbid | — | 20 | 33 | 25 | 6 | 1,3BG | None | 50/50/0 |
| 1-7 | Not Possible | Separated | — | — | — | — | — | None | PPG-7 | — |
| 1-8 | Not Possible | Separated | — | — | — | — | — | None | BPPG-13 | — |
| 1-9 | Favorable | Opaque | — | 20 | 33 | 25 | 6 | BDEG | None | 50/50/0 |
| 2-1 | Favorable | Transparent | 10000 | 20 | 33 | 25 | 6 | None | BPPG-13 | 50/0/50 |
| 2-2 | Defective | Opaque | — | 20 | 33 | 25 | — | BZL | None | 50/50/0 |
| 3-1 | Defective | Opaque | — | 20 | 52 | 10 | 6 | HG | None | 50/50/0 |
| 3-2 | Defective | Opaque | — | 20 | 52 | 10 | 6 | BDEG | None | 50/50/0 |

Based on the aforementioned results, diol compounds with a low molecular weight not corresponding to component (B) were found to be not suitable as a solvent for the (AB)n type polyether-polysiloxane block copolymer. This is because affinity with the copolymer is thought to be low, but in most cases, separation of the composition is caused. Although HG is considered to have relatively high affinity with the copolymer in this group, the compositions obtained trace amount of residual alkal components deactivate the platinum catalyst used in the hydrosilylation reaction. Furthermore, the polyglycols have a high number of ether bonds in a molecule, and therefore are easily oxidized by contact with air, and thus easily generates peroxide. Peroxide also deactivates the platinum catalyst and disrupts the catalyst cycle of hydrosilylation, and therefore, general polyglycols are accompanied by a significant disadvantage when used as a hydrosilylation reaction solvent.

Based on the aforementioned, glycol ethers that are distilled purified and having a low molecular weight and low amount of repeating units are generally sold, and therefore, there is no problem with inhibiting hydrosilylation due to impurities, the ability to compatibilize the organopolysiloxane containing a SiH group on a terminal and polyether containing a methallyl group on both terminals is high in a molecular structure, and thus the glycol ethers are considered to be useful as a reaction solvent and diluting agent of an (AB)n type polyether-polysiloxane block copolymer. Note that cases mentioning that glycol ethers having a low molecular weight and low amount of repeating units, which are component (B) of the present invention are useful as the reaction solvent and diluting agent of the (AB)n type polyether-polysiloxane block copolymer according to the present invention have not been reported within a scope investigated by the present inventors.

In addition thereto, the present inventors made further discoveries. In the related art, the glycol ethers with a low molecular weight and low amount of repeating units often have relatively similar structures and properties, and therefore are often collectively treated as a so-called "glycol ether". However, as a result of detailed examination as reaction solvent and residual diluting agent of the (AB)n type polyether-polysiloxane block copolymer, a large difference in usefulness was found between glycol ethers of an EO derivative and glycol ethers of a PO derivative. This is clear not only from the appearance of the obtained composition, but also from comparison of the GPC analysis results of Comparative Example 1-9 and Examples 1-1 and 1-2, and comparison of GPC analysis of Comparative Example 3-2 and Examples 4-1 and 4-2 as shown in the following Table 3.

TABLE 3

GPC data of several samples obtained in the examples and comparative examples (degree of polymerization n = 6 in design of the copolymer)

| Sample | Diluting agent | Hydroxyl group of diluting agent | Peak Number, Shape of Copolymer | Number average molecular weight of copolymer | Peak Area Ratio % of Unreacted Methallyl Polyether With Regard to Copolymer |
|---|---|---|---|---|---|
| Comparative Example 1-9 | BDEG | Primary | Two peaks | 20000 | 85.8 |
| Example 1-1 | BDPG | Secondary | One peak | 39300 | 11.5 |
| Example 1-2 | BPG | Secondary | One peak | 31800 | 19.8 |
| Comparative Example 3-2 | BDEG | Primary | Two peaks | 26200 | 23.2 |
| Example 4-1 | BDPG | Secondary | One peak | 46100 | 8.6 |
| Example 4-2 | BPG | Secondary | One peak | 40200 | 11.3 |

The measurement conditions in the aforementioned GPC analysis are as follows.
"GPB Measurement Conditions"
Eluent: Chloroform (reagent special grade)
Measurement temperature: 40° C.
Detector: Refractometer (peak detection on plus side)
Flow rate: 1.0 mL/min
Calibration: Performed by standard polystyrene
Injection amount of sample solution: 100 μL (sample concentration: 1 wt %)

In other words, if BDEG having a primary hydroxyl group was used as the reaction solvent, a copolymer with a high molecular weight was not obtained, and the ratio of unreacted and remaining polyethers containing a methallyl group on both terminals was high. On the other hand, if BPDG and BPG having a secondary hydroxyl group were used as the reaction solvent, a copolymer with a molecular weight exceeding 30000, used as measure for exhibiting performance as a foam stabilizing agent for polyurethane microcellular foam was obtained, and the ratio of unreacted and remaining polyethers containing a methallyl group on both terminals was low. In the case of the former, reactivity of the primary hydroxyl group is high, and therefore, this was considered to be a copolymer with a low molecular weight far from design where the ratio of block terminals of the organopolysiloxane containing a SiH group on both terminals is unignorably high. In other words, glycol ethers with a low molecular weight and low amount of repeating units, where the terminal hydroxyl group is secondary was clearly specifically useful in an application according to the present invention.

Next, the present inventors predicted that even with a monool organic compound having a primary hydroxyl group, a reaction of the hydroxyl group (corresponding to the side reaction in the case of the present invention) was less likely to occur with a compound having high hydrophobicity or a compound having a bulky substitution group near a carbon atom where a hydroxyl group is bonded, and thought that a substance was available as a hydrosilylation reaction solvent and residual diluting agent according to the present invention. Considering low melting point properties (convenience where the polyether-polysiloxane block copolymer composition does not easily solidify even in the winter), compatibility performance, ease of availability at an industrial production scale, cost, and the like desired as a diluting agent, benzyl alcohol and a liquid higher alcohol compound having a branched alkyl group with 12 to 24 carbon atoms were taken and tested. As a result, only the former case (Example 2-5) was surprisingly discovered to have an effect that achieves the objective. The following table 4 shows the results of GPC measuring the polyether-polysiloxane block copolymer composition (Example 2-5) according to the present invention, obtained in this manner, under the same conditions as described above.

TABLE 4

GPC data of several samples obtained in the examples and comparative examples (degree of polymerization n > 10, n = 6 in design of the copolymer)

| Sample | Reaction Catalyst | Diluting agent | Methallyl/ Si—H Molar Ratio | Number average molecular weight of copolymer | Peak Area Ratio % of Unreacted Methallyl Polyether With Regard to Copolymer |
|---|---|---|---|---|---|
| Comparative Example 2-1 | Toluene | BPPG-13 | 1.18 (n = 6) | 46500 | 7.3 |
| Example 1-1 | | BDPG | 1.18 (n = 6) | 39300 | 11.5 |

TABLE 4-continued

GPC data of several samples obtained in the examples and comparative examples (degree of polymerization n > 10, n = 6 in design of the copolymer)

| Sample | Reaction Catalyst | Diluting agent | Methallyl/Si—H Molar Ratio | Number average molecular weight of co-polymer | Peak Area Ratio % of Unreacted Methallyl Polyether With Regard to Copolymer |
|---|---|---|---|---|---|
| Example 2-1 | BDPG | | Approximately 1.0 | 57900 | 6.3 |
| Example 2-2 | BPG | | Approximately 1.0 | 40300 | 12.5 |
| Example 2-3 | None | BDPG | Approximately 1.0 | 102000 | 1.5 |
| Example 2-5 | HDL | | Approximately 1.0 | 62900 | 5.0 |

Based on the aforementioned results, liquid higher alcohol compounds having a branched alkyl group with 12 to 24 carbon atoms were also confirmed to be useful as a reaction solvent and diluting agent of the polyether-polysiloxane block copolymer according to the present invention. Furthermore, by comparing Examples 1-1 and 2-1, it is confirmed that the molar ratio of the polyether containing a methallyl group on both terminals with regard to the organopolysiloxane containing a SiH group on both terminals can be adjusted to control the molecular weight of the copolymer within a practical range as a microcellular foam stabilizing agent.

Next, the present inventors tested a solution by the composition of the present invention for problems of limiting use in a urethane foam formulation (such as soft foam or the like) where open cell ratio adjustment or making an open cell is desired, based on a trend where an (AB)n copolymer indicated in Patent Literature 10 (JP 2010-539280 T) forms a hydrogel in the presence of water. Specifically, Examples 1-1 was taken as the polyether-polysiloxane block copolymer composition of the present invention, and Comparative Example 2-1 was taken as the (AB)n type polyether-polysiloxane block copolymer according to technology in the related art (Patent Literature 6: JP 08-156143 A), and a miscibility test of both with water was performed. The test method is shown below.

50 g of the polyether-polysiloxane block copolymer composition and 50 g of water were inserted in a 200 mL glass bottle, and then mixing was performed at 1600 rpm×5 minutes using a homodisper at room temperature. The properties immediately after preparing the obtained mixture and properties after allowing to stand for one day at room temperature were observed and recorded. The drastic results discovered herein are shown in the following Table 5.

TABLE 5

Results of water miscibility test

| Sample | Co-polymer % | Diluting agent % | Water % | Properties Immediately After Preparing | Properties One Day Later |
|---|---|---|---|---|---|
| Comparative Example 2-1 | 25% | BPPG-13 25% | 50% | Entire body is a dark white powdered solid gel | Entire body is a dark white powdered solid gel |
| Example 1-1 | 25% | BDPG 25% | 50% | Semi-transparent homogeneous liquid with favorable fluidity | Small amount of creaming at the top, but favorable fluidity |

Based on the aforementioned results, the polyether-polysiloxane block copolymer composition of the present invention was verified to completely resolve the hydrogel forming problem due to contact with water, which occurred with a (AB)n type polyether-polysiloxane block copolymer in the related art. Furthermore, forming the aforementioned composition by combining the polyether-polysiloxane block copolymer (A) and component (B) according to the present invention was clearly a key to resolving the problem. Therefore, the polyether-polysiloxane block copolymer composition of the present invention can be widely used for urethane foam formulations (such as soft foam or the like) where open cell ratio adjustment or making an open cell is desired.

Furthermore, the present inventors added several picked up samples to a hard urethane foam formulation to perform a foaming test, based on the knowledge with regard to the tendency of the type of polyurethane foam and molecular weight of the polyether-modified silicone suitable thereto. A composition with a relatively low molecular weight was selected as the polyether-polysiloxane block copolymer composition (sample) according to the present invention, and then compared with Comparative Example 2-1 which is an (AB)n type polyether-polysiloxane block copolymer composition based on technology in the related art (Patent Literature 6: JP 08-156143 A). The tested hard foam formulation is shown below.

TABLE 6

Hard polyurethane foam-forming composition

| Component | | Content | Amount of Added Parts | wt. % |
|---|---|---|---|---|
| Components for Premixing | Polyol | Sorbitol-based polyether polyol (Hydroxyl group value: 450) | 100 | 32.62 |
| | Tertiary amine catalyst | $Me_2N$—$(CH_2)_6$—$NMe_2$ | 1.8 | 0.59 |
| | Water | (Foaming agent) * | 6.0 | 1.96 |
| | Polyether-polysiloxane block copolymer composition | Surfactant | 1.0 | 0.33 |
| Isocyanate | | Polymethylene polyphenyl polyisocyanate (index: 110, NCO % = 31.5) | 197.8 | 64.50 |
| Total | | | 306.6 | 100.00 |

* Carbon dioxide gases generated due to a reaction with isocyanate

Formation of Hard Polyurethane Foam

The polyurethane foam-forming composition of the present invention was adjusted and the polyurethane foam was formed at a scale where the total amount was 16.7% in Table 6. Note that operations were performed in a thermostatic chamber at approximately 25° C., and all raw materials were used from a condition achieved at a constant temperature.

A polyol, water, catalyst, and surfactant were accurately weighed in a 200 mL polycup, and then stirred at 3500 rpm for 15 seconds using a disk blade type disper mixer.

Thereafter, isocyanate was added to the premixed solution mixed in advanced, and then mixed at 3500 rpm for 7 seconds using the same blade.

A uniformly mixed urethane foam-forming composition was poured into a 1 L paper cup over 8 seconds to allow free foaming.

The composition was allowed to stand for 40 to 60 minutes as is in a thermostatic chamber.

After two hours, the foam was cut in half from above, and then the foam height and cell structure of the cut surface were observed and recorded.

TABLE 7

Evaluation results of hard polyurethane foam

| Type of Surfactant | Number average molecular weight of copolymer | Diluting agent (50% Included in Surfactant) | Foam Height cm | Cell Structure |
|---|---|---|---|---|
| Comparative Example 2-1 | 46500 | BPPG-13 | 19 | Rough |
| Example 1-1 | 39300 | BDPG | 19 | Fine |
| Example 1-2 | 31800 | BPG | 19 | Fine |

Based on the aforementioned results, the polyether-polysiloxane block copolymer composition according to the present invention was confirmed to have an excellent effect as a surfactant or foam stabilizing agent for hard polyurethane foam.

Finally, Table 8 shows foam formulation examples of a microcellular polyurethane foam-forming composition, and simply shows manufacturing processes thereof.

Examples of Manufacturing Processes

1) The premixed solution and isocyanate (at an amount where the isocyanate index is 107) is stirred and mixed for 1 minute using a dynamic mixer while feeding nitrogen gas, and then injecting as is in a mold.
2) After primary curing for 30 minutes at 160° C., secondary curing is performed for 4 hours at 110° C.
3) Thereafter, A metal shaft is press-fitted and adhered thereto, and end portions are cut, surfaces are polished, and the like to obtain microcellular polyurethane foam.

Expected Effects

The polyurethane foam according to the present invention does not include residual substances such as nonreactive dodecyl benzene in the foam stabilizer (foam stabilizing agent), and therefore, problems such as migration (oozing) in the obtained microcellular foam is less likely to occur. Diluting agent included in the foam stabilizing agent of the present invention: Component (B) has appropriate reactivity and volatility in the urethane foam formulation, and therefore, an increase in cell opening function (forming flexible foam with high air permeability) due to a volatilization effect is expected in Formulation Examples 1 and 2, for example. Furthermore, formation of a foam with excellent strength and low air permeability due to contributing increasing foam crosslinking density is expected in Formulation Example 4 using a foam stabilizing agent where the amount of component (B) used is reduced and nonvolatile PPG-7 is added. Formation of physical foam with an intermediate balance in physical properties with the two previous examples is expected in Formulation Example 4.

The invention claimed is:

1. A polyether-polysiloxane block copolymer composition, comprising the following component (A) and component (B) at a mass ratio of (A)/(B)=10/90 to 90/10, and not containing a dimethyl polysiloxane at more than the mass of component (A):

(A) a polyether-polysiloxane block copolymer having a terminal group (—Z) and having in a molecule structural units as expressed by General Formula (1):

TABLE 8

Examples of microcellular polyurethane foam-forming compositions

| Component Type | | Content | Formulation Example 1 | Formulation Example 2 | Formulation Example 3 | Formulation Example 4 |
|---|---|---|---|---|---|---|
| Premixing Components | Polymer polyol (hydroxyl group value: 33) | Polymer particle dispersion obtained by polymerizing acrylonitrile styrene in polyol | 100 | 100 | 100 | 100 |
| | Catalyst | Product diluted 10 times with nickel acetyl acetate | 2.0 | 2.0 | 2.0 | 2.0 |
| | Foam Stabilizing agent | Example 1-1 | 10 | — | — | — |
| | | Example 2-1 | — | 10 | — | — |
| | | Example 5-2 | — | — | 15 | — |
| | | Example 5-3 | — | — | — | 20 |
| Isocyanate | Modified MDI | Carbodiimide-modified MDI, NCO % = 29.0 | 15.8 | 15.8 | 15.8 | 15.8 |
| | | Total | 127.8 | 127.8 | 132.8 | 137.8 |

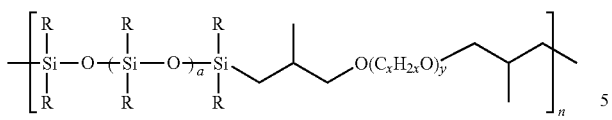

where each R individually represents a monovalent hydrocarbon group with 1 to 9 carbon atoms, which does not have an aliphatic unsaturated bond; x represents a number of from 2 to 4; a represents a number of from 1 to 200; y represents a number where the molecular weight of a polyether portion as expressed by $(C_xH_{2x}O)_y$ is within a range of 400 to 5000; and n represents a number of at least 2, wherein the terminal group (—Z) is at least one type of functional group selected from $Z^1$: alkenyl groups, hydroxyl groups, alkoxy groups, or acetoxy groups bonded to a polyether portion; and $Z^2$: monovalent hydrocarbon groups that do not have a hetero atom, hydroxyl groups, or alkoxy groups, bonded to a silicon atom;

(B) one or two or more types of monool organic compounds selected from (B1) or (B2), which is a liquid at 5° C., has one alcoholic hydroxyl group in a molecule, and does not contain a hetero atom other than oxygen:

(B1) glycol ether compounds where a terminal hydrogen is substituted by a hydrocarbon group with 1 to 8 carbon atoms, where a secondary alcoholic hydroxyl group is provided on another terminal, and having 1 to 3 oxyalkylene units with 2 to 4 carbon atoms, and (B2) higher alcohol compounds having a branched alkyl group with 12 or more carbon atoms; and further comprising:

(C) at least one type of polyalkylene glycol having hydroxyl groups on both terminals of a molecular chain or a derivative thereof, which is a liquid at 25° C., where the derivative is a polyalkylene glycol having one terminal hydroxyl group substituted by a hydrocarbon group with 1 to 8 carbon atoms selected from alkyl, aralkyl, and aryl groups, and wherein each of the polyalkylene glycol and the derivative thereof has 4 to 50 repeating oxyalkylene units with 2 to 4 carbon atoms, within a range of 10 to 300 parts by mass with regard to a total of 100 parts by mass of component (A) and component (B).

2. The polyether-polysiloxane block copolymer composition according to claim 1, wherein component (A) is a polyether-polysiloxane block copolymer obtained by hydrosilylation reaction of:

an organopolysiloxane containing a SiH group on both terminals as expressed by General Formula (2):

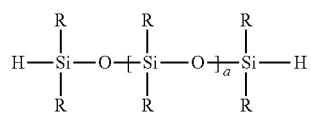

where R represents the same groups as described above, and a represents the same numbers as described above; and a polyether containing a methallyl group on both terminals as expressed by General Formula (3):

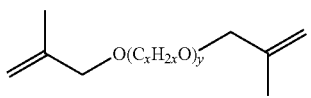

where x and y represent the same numbers as described above; and having structural units as expressed by General Formula (1):

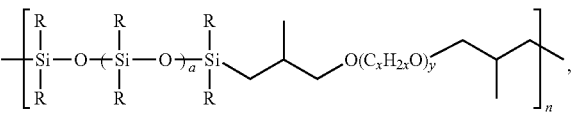

where R represents the same groups as described above, and x, a, y, and n represent the same numbers as described above.

3. The polyether-polysiloxane block copolymer composition according to claim 1, wherein component (B) is one or two or more types of monool organic compound selected from propylene glycol monobutyl ethers, dipropylene glycol monobutyl ethers, tripropylene glycol monobutyl ethers, propylene glycol monomethyl ethers, dipropylene glycol monomethyl ethers, tripropylene glycol monomethyl ethers, propylene glycol mono(iso)propyl ethers, dipropylene glycol mono(iso)propyl ethers, tripropylene glycol mono(iso)propyl ethers, propylene glycol monoethyl ethers, dipropylene glycol monoethyl ethers, tripropylene glycol monoethyl ethers, 2-butyl-1-octanols, 2-hexyl-1-decanols, 2-octyl-1-dodecanols, isostearyl alcohols, and 2-decyl-1-tetradecanols.

4. The polyether-polysiloxane block copolymer composition according to claim 1, wherein the mass ratio of component (A) and component (B) is within a range of 20/80 to 70/30.

5. The polyether-polysiloxane block copolymer composition according to claim 1, wherein the viscosity of the entire composition at 25° C. is within a range of 100 to 35000 mm²/s.

6. A surfactant comprising the polyether-polysiloxane block copolymer composition according to claim 1.

7. A foam stabilizer comprising the polyether-polysiloxane block copolymer composition according to claim 1.

8. A polyurethane foam-forming composition comprising the polyether-polysiloxane block copolymer composition according to claim 1.

9. A polyurethane foam-forming composition, comprising:

(a) a polyol;
(b) a polyisocyanate;
(c) a catalyst;
(d) a foam stabilizer containing the polyether-polysiloxane block copolymer composition according to claim 1; and
(e) optionally, at least one added component selected from a group consisting of foam stabilizers other than component (d), foaming agents, diluting agents, chain extenders, crosslinking agents, water, nonaqueous foaming agents, fillers, reinforcing agents, pigments, dyes, coloring agents, flame retardants, antioxidants, anti-ozone agents, UV stabilizers, antistatic agents, disinfectants, and antibacterial agents.

10. The polyurethane foam-forming composition according to claim 9, comprising 0.5 to 8.0 parts by mass of the polyether-polysiloxane block copolymer (A), in the polyether-polysiloxane block copolymer composition of (d) the foam stabilizer, with regard to 100 parts by mass of (a) the polyol.

11. Polyurethane foam obtained from the polyurethane foam-forming composition according to claim 8, optionally wherein the polyurethane foam is hard foam, semi-hard foam, soft foam, or microcellular foam.

12. Cosmetic raw material comprising the polyether-polysiloxane block copolymer composition according to claim 1.

13. A cosmetic comprising the polyether-polysiloxane block copolymer composition according to claim 1.

14. A method of manufacturing the polyether-polysiloxane block copolymer composition according to claim 2, said method comprising:
   initiating a hydrosilylation reaction between the organopolysiloxane as expressed by General Formula (2) and the polyether as expressed by General Formula (3), without a solvent; and
   diluting or promoting the reaction by adding component (B).

15. A method of manufacturing the polyether-polysiloxane block copolymer composition according to claim 2, said method comprising:
   initiating or advancing a hydrosilylation reaction between the organopolysiloxane as expressed by General Formula (2) and the polyether as expressed by General Formula (3), in the presence of component (B).

16. A method of manufacturing the polyether-polysiloxane block copolymer composition according to claim 2, said method comprising:
   initiating or advancing a hydrosilylation reaction between the organopolysiloxane as expressed by General Formula (2) and the polyether as expressed by General Formula (3), in the presence of a volatile organic solvent (B') which is different from component (B); and
   solvent exchanging the volatile organic solvent (B') with component (B).

17. The method of manufacturing a polyether-polysiloxane block copolymer composition according to claim 14, free of a stripping step.

18. The method of manufacturing a polyether-polysiloxane block copolymer composition according to claim 15, free of a stripping step.

19. The polyether-polysiloxane block copolymer composition according to claim 1, wherein in General Formula (1) of component (A), a represents a number within a range of from 10 to 45, y represents a number where the molecular weight of a polyether portion as expressed by $(C_xH_{2x}O)_y$ is within a range of 2000 to 5000, and the mass ratio of an oxyethylene $(C_2H_4O)$ unit configuring the entire polyether portion is within a range of 35 to 90% on average.

20. The polyether-polysiloxane block copolymer composition according to claim 19, wherein the viscosity of the entire composition at 25° C. is within a range of 100 to 35000 mm²/s.

* * * * *